United States Patent [19]
Afonso et al.

[11] Patent Number: 5,958,939
[45] Date of Patent: Sep. 28, 1999

[54] TRICYCLIC COMPOUNDS USEFUL FOR INHIBITION OF A G-PROTEIN FUNCTION AND FOR TREATMENT OF PROLIFERATIVE DISEASES

[75] Inventors: Adriano Afonso, West Caldwell; Joseph M. Kelly, Parlin; Ronald L. Wolin, Westfield, all of N.J.

[73] Assignee: Schering Corporation, Kenilworth, N.J.

[21] Appl. No.: 08/891,849

[22] Filed: Jul. 10, 1997

Related U.S. Application Data

[62] Division of application No. 08/410,442, Mar. 24, 1995, Pat. No. 5,684,013.

[51] Int. Cl.$^6$ .................. C07D 401/04; C07D 403/04; A61K 31/445
[52] U.S. Cl. ............................. 514/290; 546/93
[58] Field of Search ................... 546/93; 514/290

[56] References Cited

U.S. PATENT DOCUMENTS

| | | | |
|---|---|---|---|
| 4,282,233 | 8/1981 | Villani | 514/290 |
| 4,826,853 | 5/1989 | Piwinski et al. | 514/290 |
| 4,831,042 | 5/1989 | Villani | 514/316 |
| 4,863,931 | 9/1989 | Schumacher et al. | 514/290 |
| 5,089,496 | 2/1992 | Piwinski et al. | 514/253 |
| 5,104,876 | 4/1992 | Piwinski et al. | 514/254 |
| 5,141,851 | 8/1992 | Brown et al. | 435/15 |
| 5,151,423 | 9/1992 | Piwinski et al. | 514/254 |

FOREIGN PATENT DOCUMENTS

| | | |
|---|---|---|
| 0042544 | 12/1981 | European Pat. Off. |
| 0270818 | 6/1988 | European Pat. Off. |
| 0396083 | 11/1990 | European Pat. Off. |
| 0495484 | 7/1992 | European Pat. Off. |
| 0535730 | 4/1993 | European Pat. Off. |
| WO88/03138 | 5/1988 | WIPO |
| WO89/10363 | 11/1989 | WIPO |
| WO90/13548 | 11/1990 | WIPO |
| WO92/00293 | 1/1992 | WIPO |
| WO92/11034 | 7/1992 | WIPO |
| WO94/04561 | 3/1994 | WIPO |
| WO94/24107 | 10/1994 | WIPO |

OTHER PUBLICATIONS

Cell, 65, 1–4 (1991).
J. Biol. Chem., 266, (24) 15575–15578 (1991).
Proc. Natl. Acad. Sci. USA, 87, 3042–3046 (1990).
Proc. Natl. Acad. Sci. USA, 88, 8631–8635 (1991).
Nature, 356, 713–715 (1992).
Proc. Natl. Acad. Sci. USA, 87, 7541–7545 (1990).
J. Biol. Chem., 265, (25) 14701–14704 (1990).
Proc. Natl. Acad. Sci. USA, 87, 7926–7929 (1990).
Cell, 62, 81–88 (1990).
Piwinski, et al., J. Med. Chem., 34, (1) 457–461 (1991).
Chem. Abstracts No. 121:53129x (1994) for WO94/04561.
Masci, J. Chem. Soc., Chem. Commun., 1262–1263 (1982).
Masci, J. Org. Chem., 50, 4081–4087 (1985).
Sebti, et al., Proc. Ann. Meeting AM Assoc. Cancer Res., 33:A2217 (1992).
Villani, et al., J. Med. Chem., 15, (7) 750–754 (1972).
Billah, et al., Lipids, 26, (12) 1172–1174 (1991).
Villani, et al., Arzneim.–Forsch./Drug Res., 36(II), 1311–1314 (1986).

Primary Examiner—Alan L. Rotman
Attorney, Agent, or Firm—Henry C. Jeanette

[57] ABSTRACT

A method of inhibiting Ras function and therefore inhibiting cellular growth is disclosed. The method comprises the administration of a novel compound of the formula (Ia), (Ib) or (Ic)

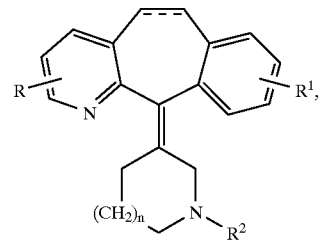

(Ia)

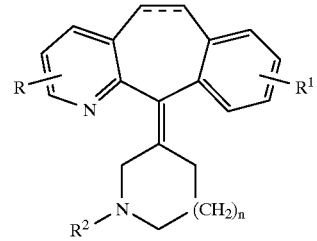

(Ib)

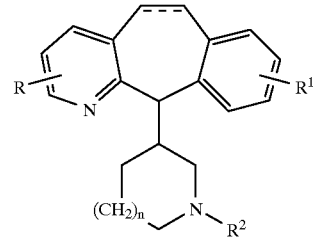

(Ic)

wherein:

R and $R^1$ are H, alkyl, halogeno, OH, alkoxy, $NH_2$, alkylamino, dialkylamino, $CF_3$, $SO_3H$, $CO_2R^3$, $NO_2$, $SO_2NH_2$, or $CONHR^4$;

n is 0 or 1;

$R^2$ is a group of the formula $R^5C(O)$—, $R^5CH_2C(O)$—, $R^5C(R^6)_2C(O)$—, $R^5SO_2$—, $R^5CH_2SO_2$—, $R^5SCH_2C(O)$—, $R^5OC(O)$—, $R^5NHC(O)$—, $R^5C(O)C(O)$— or $R^5SC(O)$—;

$R^5$ is alkyl, aryl, arylalkyl, arylalkenyl, heteroaryl, heteroarylalkyl, heteroarylalkenyl or heterocycloalkyl; and $R^6$ is alkyl or $C(R^6)_2$ is a carbocyclic ring;

or pharmaceutically aceptable salts thereof.

8 Claims, No Drawings

TRICYCLIC COMPOUNDS USEFUL FOR INHIBITION OF A G-PROTEIN FUNCTION AND FOR TREATMENT OF PROLIFERATIVE DISEASES

This is a division of application Ser. No. 08/410,442, filed Mar. 24, 1995, now U.S. Pat. No. 5,684,013.

BACKGROUND

International Publication Number WO92/11034, published Jul. 9, 1992, discloses a method of increasing the sensitivity of a tumor to an antineoplastic agent, which tumor is resistant to the antineoplastic agent, by the concurrent administration of the antineoplastic agent and a potentiating agent of the formula:

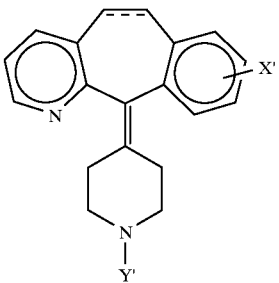

wherein the dotted line represents an optional double bond, X' is hydrogen or halo, and Y' is hydrogen, substituted carboxylate or substituted sulfonyl. For example, Y' can be, amongst others, —COOR' wherein R' is C1 to C6 alkyl or substituted alkyl, phenyl, substituted phenyl, C7 to C12 aralkyl or substituted aralkyl or -2, -3, or -4 piperidyl or N-substituted piperidyl. Y' can also be, amongst others, $SO_2R'$ wherein R' is C1 to C6 alkyl, phenyl, substituted phenyl, C7 to C12 aralkyl or substituted aralkyl. Examples of such potentiating agents include 11-(4-piperidylidene)-5H-benzo[5,6]cyelohepta[1,2-b]pyridines such as Loratadine.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To acquire transforming potential, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as anti-cancer agents for tumors in which Ras contributes to transformation. Mutated, oncogenic forms of ras are frequently found in many human cancers, most notably in more than 50% of colon and pancreatic carcinomas (Kohl et al., Science, Vol. 260, 1834 to 1837, 1993).

In view of the current interest in inhibitors of farnesyl protein transferase, a welcome contribution to the art would be compounds useful for the inhibition of farnesyl protein transferase. Such a contribution is provided by this invention.

SUMMARY OF THE INVENTION

This invention provides a method for inhibiting farnesyl protein transferase (FPT) using the tricyclic compounds described below which: (i) potently inhibit FPT, but not geranylgeranyl protein transferase I, in vitro: (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

This invention also provides a method for inhibiting the abnormal growth of cells, including transformed cells, by administering an effective amount of a compound of the present invention. Abnormal growth of cells means cell growth independent of normal regulatory mechanisms (e.g., loss of contact inhibition), including the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

This invention provides compounds of the formula (Ia), (Ib) and (Ic)

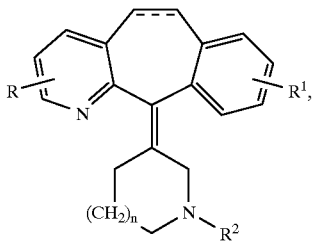

(Ia)

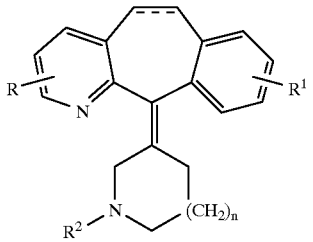

(Ib)

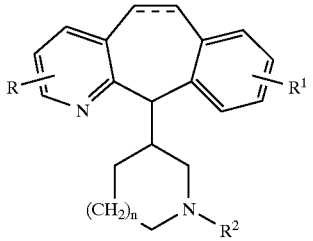

(Ic)

wherein:
R and $R^1$ are independently selected from H, $(C_1-C_6)$ alkyl, halogeno, OH, $(C_1-C_6)$alkoxy; $NH_2$; $(C_1-C_6)$ alkylamino; di$((C_1-C_6)$alkyl)amino; $CF_3$; $SO_3H$; $CO_2R^3$; $NO_2$; $SO_2NH_2$; and $CONHR^4$;
$R^2$ is $R^5C(O)$—, $R^5CH_2C(O)$—, $R^5C(R^6)_2C(O)$—, $R^5SO_2$—, $R^5CH_2SO_2$—, $R^5SCH_2C(O)$—, $R^5OC(O)$—, $R^5NHC(O)$—, $R^5C(O)C(O)$— or $R^5OC(S)$—;
$R^3$ is $(C_1-C_6)$alkyl, aryl;
R is $(C_1-C_6)$alkyl;
$R^5$ is $(C_1-C_6)$alkyl, aryl, aryl$(C_1-C_6)$alkyl, aryl$(C_2-C_6)$ alkenyl, heteroaryl, heteroaryl$(C_1-C_6)$alkyl, heteroaryl $(C_2-C_6)$alkenyl or heterocycloalkyl;

Each $R^6$ independently represents $(C_1-C_6)$alkyl, or both $R^4$ groups together with the carbon atom to which they are attached comprise a $(C_3-C_7)$carbocyclic ring;

n is 0 or 1;

the dotted line represents an optional double bond; and pharmaceutically acceptable salts thereof.

This invention also provides a method for inhibiting tumor growth by administering an effective amount of the tricyclic compounds, described herein, to a mammal (e.g., a human) in need of such treatment. In particular, this invention provides a method for inhibiting the growth of tumors expressing an activated Ras oncogene by the administration of an effective amount of the above described compounds. Examples of tumors which may be inhibited include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, bladder carcinoma, and myelodysplastic syndrome (MDS).

It is believed that this invention also provides a method for inhibiting proliferative diseases, both benign and malignant, wherein Ras proteins are aberrantly activated as a result of oncogenic mutation in other genes—i.e., the Ras gene itself is not activated by mutation to an oncogenic form—with said inhibition being accomplished by the administration of an effective amount of the tricyclic compounds described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, lyn, fyn), may be inhibited by the tricyclic compounds described herein.

The compounds of this invention inhibit farnesyl protein transferase and the farnesylation of the oncogene protein Ras. This invention further provides a method of inhibiting ras farnesyl protein transferase, in mammals, especially humans, by the administration of an effective amount of the tricyclic compounds described above. The administration of the compounds of this invention to patients, to inhibit farnesyl protein transferase, is useful in the treatment of the cancers described above.

The tricyclic compounds useful in the methods of this invention inhibit abnormal cellular growth. Without wishing to be bound by theory, it is believed that these compounds may function through the inhibition of G-protein function, such as ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

DETAILED DESCRIPTION OF THE INVENTION

As used herein, the following terms are used as defined below unless otherwise indicated:

"alkyl", including the alkyl portions of alkoxy, alkylamino and dialkylamino, means a straight or branched carbon chain containing from one to twenty carbon atoms, preferably one to six carbon atoms;

"alkenyl" means an alkyl group containing one or two double bonds;

"heterocycloalkyl" means a saturated carbocyclic ring containing from 3 to 7 carbon atoms, preferably from 4 to 6 carbon atoms, which carbocyclic ring is interrupted by 1 to 3 heteroatoms selected from O, S and N, and includes heterocycloalkyls such as 2- or 3-tetrahydrofuranyl, 2-, 3- or 4-tetrahydropyranyl, 2- or 3- tetrahydrothienyl, 2-, 3- or 4-piperidinyl, 2- or 3-pyrrolidinyl, 2- or 3-piperizinyl and 2- or 3-dioxanyl;

"aryl" represents a carbocyclic aromatic group containing from 6 to 10 carbon atoms, such as phenyl or naphthyl, said carbocyclic group being optionally substituted with 1–3 substituents selected from halogeno, $(C_1-C_6)$alkyl, hydroxy, $(C_1-C_6)$alkoxy, phenoxy, $CF_3$, amino, alkylamino, dialkylamino, $CH_3C(O)NH—$, $CH_3C(O)O—$, $NO_2$ and $—COOR^8$, wherein $R^8$ is H or $(C_1-C_6)$alkyl;

"halogeno" means fluoro, chloro, bromo and iodo; and

"heteroaryl" means a cyclic aromatic group, containing 5 to 10 ring members, comprising 2 to 9 carbon atoms and 1 to 3 heteroatoms selected from O, S, N and N→O, wherein N→O represents an N-oxide, and includes heteroaryls such as 2-, 3- or 4-pyridyl, 2-, 3- or 4- pyridyl N-oxide, imidazolyl, triazolyl, thienyl and furanyl, which heteroaiyl group is optionally substituted by 1 to 3 substituents selected from halogeno, $(C_1-C_6)$alkyl, $(C_1-C_6)$alkoxy, amino, alkylamino, dialkylamino, $C_6H_5C(O)NHCH_2$-and $—COOR^8$, wherein $R^8$ is H or $(C_1-C_6)$alkyl.

Lines drawn into the ring systems indicate that the indicated bond may be attached to any of the substitutable ring carbon atoms.

Certain compounds of the invention may exist in different isomeric forms (e.g., enantiomers and diastereoisomers). The invention contemplates all such isomers both in pure form and in admixture, including racemic mixtures. Enol forms are also included.

The compounds of the invention can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

The following compounds and reagents are referred to herein the abbreviations indicated: trifluoroacetic anhydride (TFAA); 4-dimethylaminopyridine (DMAP); methanol (MeOH; ethanol (EtOH); diethyl ether (Et$_2$O); triethylamine (Et$_3$N); ethyl acetate (EtOAc); acetic acid (HOAc); m-chloroperbenzoic acid (MCPBA); dicyclohexylcarbodiimide (DCC); 1-(3-dimethylaminopropyl)-3-ethylcarbodiimide hydrochloride (DEC); 1-hydroxybenzotriazole (HOBT); N-methylmorpholine (NMM); dimethylformamide (DMF)

Compounds of the formula (Ia) and (Ib) can be prepared by the process shown in Reaction Scheme 1.

REACTION SCHEME 1

Step (a):

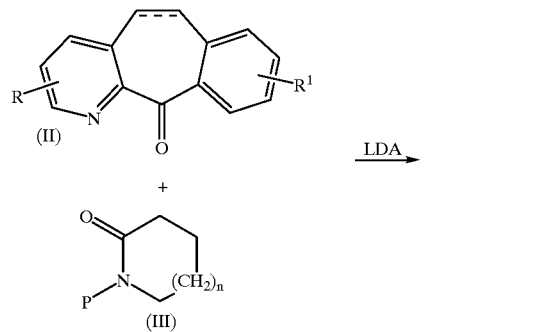

Step (b):

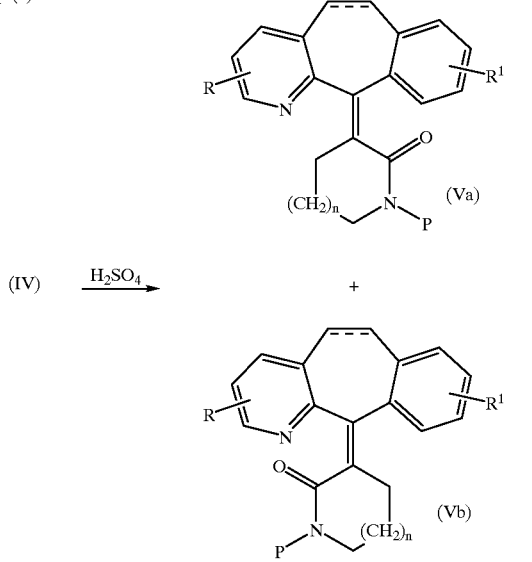

Step (c):

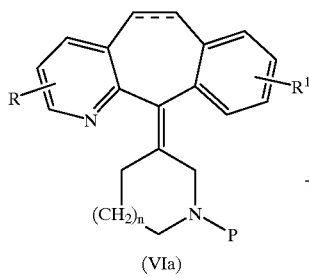

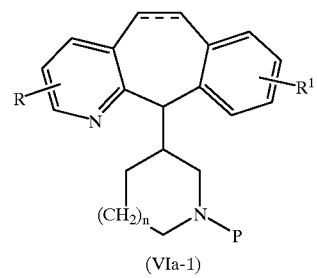

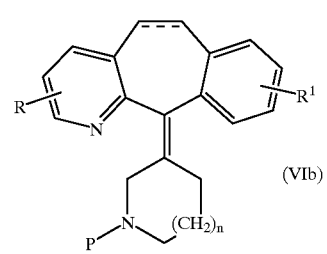

Step (d):

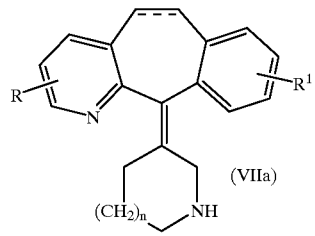

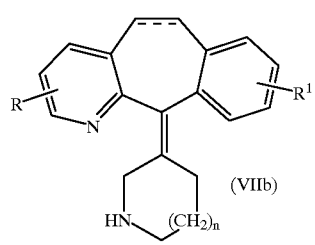

Step (e):

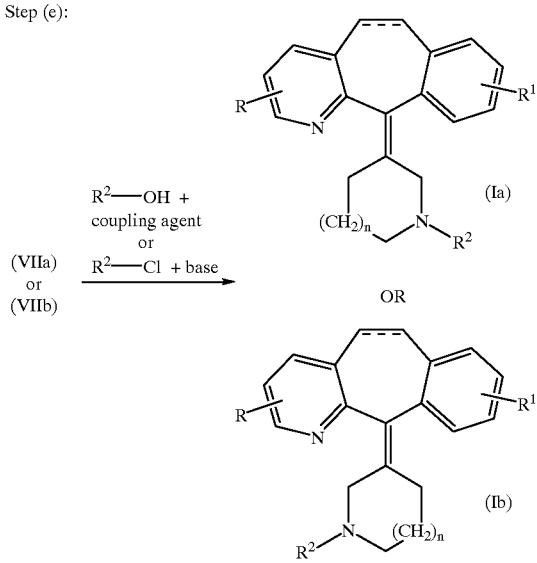

In Step (a) of Reaction Scheme 1, A protected lactam of the formula (III), wherein P is an amine protecting group, such as $CH_3$, benzyl or $C_6H_5SO_2$—, and n is as defined above, is treated with LDA, then reacted with a ketone of the formula (II) wherein R and $R^1$ are as defined above and the dotted line represents an optional double bond, at −100° to 0° C., preferably at −80 to −20° C., to form an alcohol of the formula (IV).

In Step (b) the alcohol (IV) from Step (a) is dehydrated by treating with concentrated $H_2SO_4$ to form a mixture of isomeric compounds (Va) and (Vb). The compounds (Va) and (Vb) are separated, e.g. by column chromatography, and a single isomer (Va) or (Vb) is used in Step (c).

In Step (c) the compound (Va) or (Vb) is treated with $LiAlH_4$, at −40° to 40° C., preferably at −10° to 20° C., and most preferably at about 0° C., in a suitable solvent, such as THF or $Et_2O$, to form a mixture compounds of the formula (VIa) and (VIa-1), or a compound of the formula (VIb), respectively.

In Step (d) the compound (VIa) or (vib) is deprotected using reagents and reaction conditions appropriate for the specific protecting group (P), such as those described in Greene, et al, "Protective Groups in Organic Synthesis, 2nd Ed.", pages 315–385, John Wiley & Sons, New York (1991), to form an amine of the formula (VIIa) or (VIIb), respectfully.

In Step (e) the amine (VIIa) or (VIIb) is reacted with a compound of the formula $R^2$—OH, wherein $R^2$ is as defined above, in a suitable solvent, such as DMF or $CH_2Cl_2$, in the presence of a coupling agent, such as DCC or DEC, to form a compound of the formula (Ia) or (Ib), respectfully.

Alternatively, the amine (VIIa) or (VIIb) is reacted with a compound of the formula $R^2$—Cl, wherein $R^2$ is as defined above, in the presence of a tertiary amine base, such as DMAP or pyridine, to form a compound of formula (Ia) or (Ib), respectfully.

Compounds of the formula (Ic) can be prepared by the process shown in Reaction Scheme 2.

REACTION SCHEME 2

Step (a):

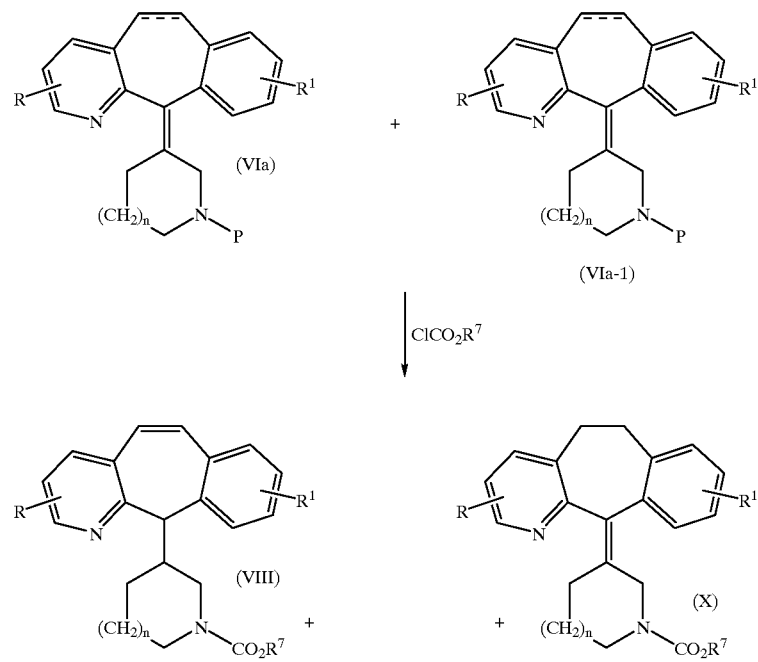

-continued

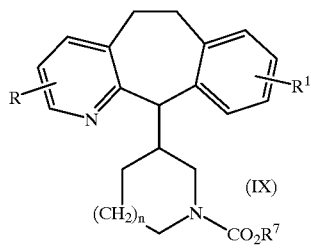

Step (b):

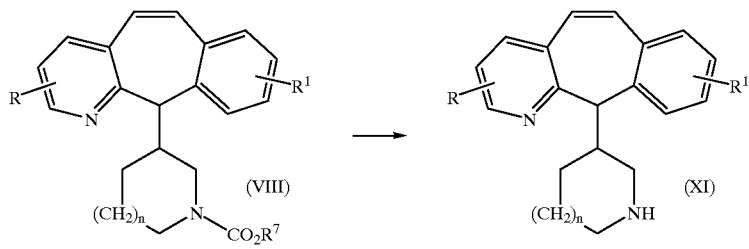

OR

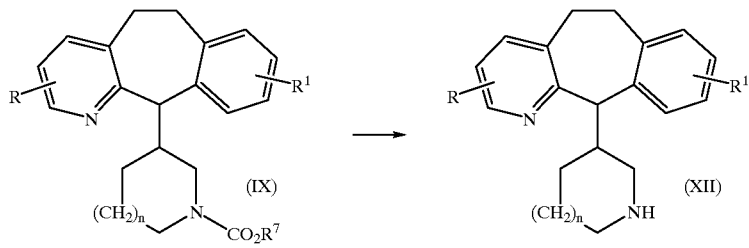

Step (c):

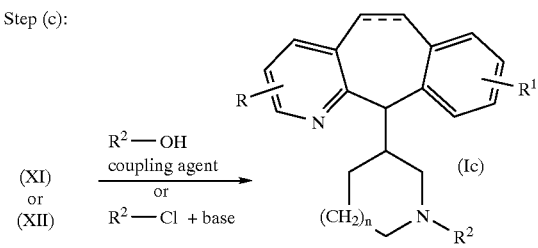

In Step (a) of Reaction Scheme 2 the mixture of compounds of the formula (VIa) and (VIa-1) from Step (c) of Reaction Scheme 1, wherein P is $CH_3$, and R, $R^1$ and n are as defined above, and the optional double bond is not present, is reacted with a compound of the formula $ClCO_2R^7$, wherein $R^7$ is ($C_1$–$C_6$)alkyl, (i.e. an alkyl chloroformate), preferably ethyl chloroformate, in the presence of a tertiary amine base, preferably $Et_3N$, in a suitable solvent, such as toluene, at 40° to 110° C., preferably at 70° to 90° C., to form a mixture of compounds (VIII), (IX) and (X). (Compounds (VIII) and (X) are fromed from compound (VIa) while compound (IXS is formed from compound (VIa-1).) Compounds (VIII), (IX) and (X) are separated, e.g. by chromatography.

In Step (b) a compound of the formula (VIII) or (IX) is reacted with concentrated HCl at 40° to 110° C., preferably at 70° to 90° C., to form an amine of the formula (XI) or (XII).

Alternatively, in Step (b) a compound of the formula (VIII) or (IX) is reacted with a hydroxide base, such as NaOH or KOH, preferably KOH, in the presence of a suitable solvent, such as a mixture of a $C_1$–$C_6$ alcohol and water, preferably a mixture of EtOH and water or iPrOH and water, at 40° to 100° C., preferably at 50° to 80° C., to form a compound of the formula (XI) or (XII), respectively.

In Step (c) a compound of the formula (XI) or (XII) is reacted with either $R^2OH$ and a coupling agent, or $R^2Cl$ and a base, via substantially the same procedures as described for Scheme 1, Step (e), to form a compound of the formula (Ic).

An alternative process for preparing compounds of the formula (Ic) is described in Reaction Scheme 3.

REACTION SCHEME 3

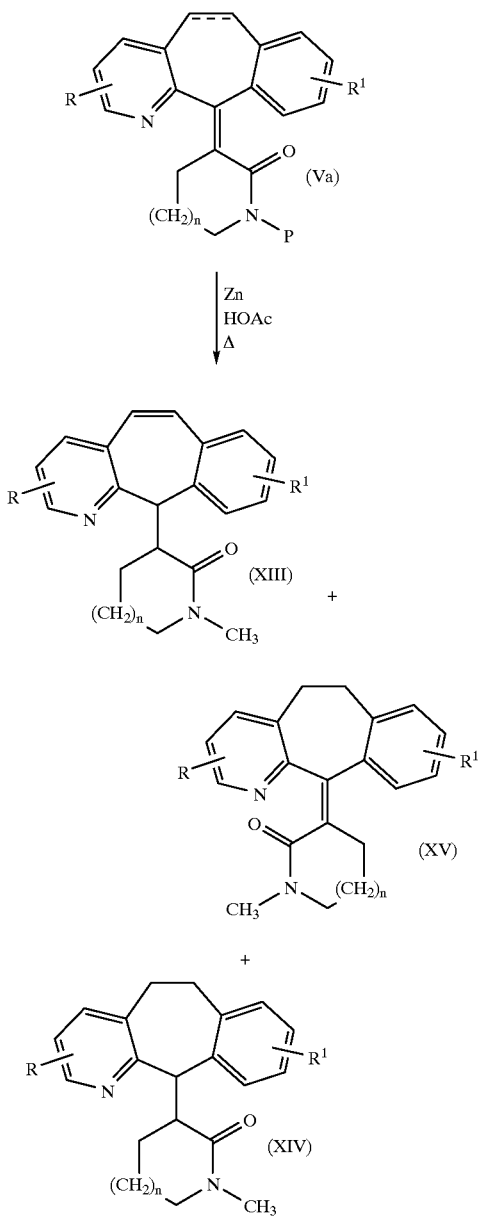

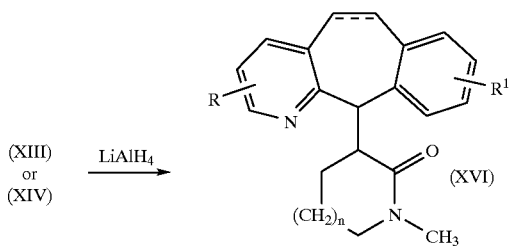

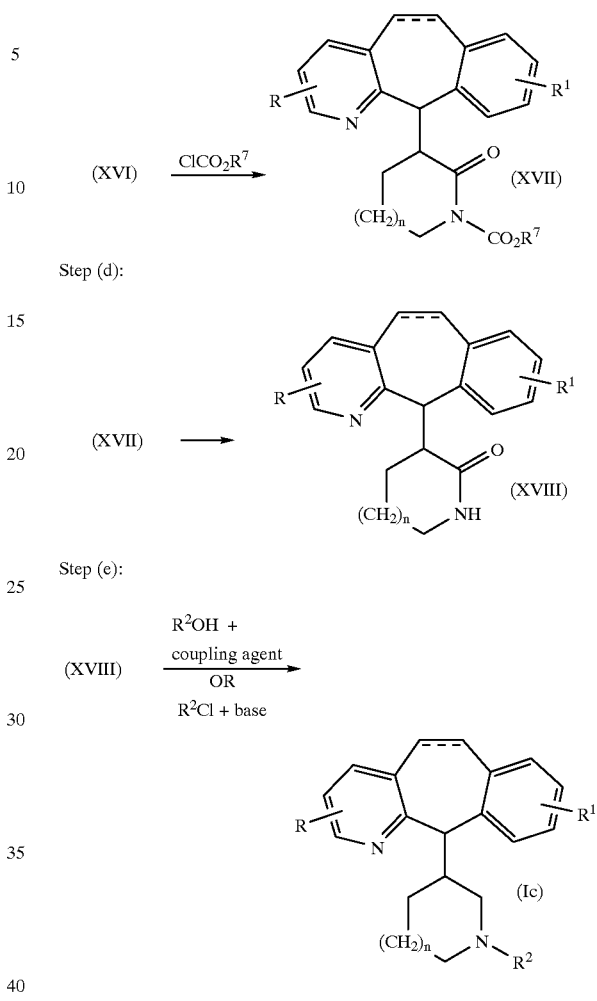

In Step (a) of Reaction Scheme 3, a compound of the formula (va) from Step (b) of Reaction Scheme 1, wherein P is $CH_3$, and R, $R^1$ and n are as defined above, and the optional double bond is not present, is reacted with Zn powder and glacial HOAc at 80° to 120° C., preferably at about 100° C., to form a mixture of compounds (XIII), (XIV) and (XV). Compounds (XIII), (XIV) and (XV) are separated, e.g. by chromatography.

In Step (b) of Reaction Scheme 3, a compound of the formula (XIII) or (XIV) is reduced by treating with a hydride reducing agent, such as LiAlH, via substantially the same procedure as described for Step (c) of Reaction Scheme 1 to form a compound of the formula (XVI), wherein R, $R^1$ and n are as defined above, and the dotted line represents an optional double bond.

In Step (c), a compound of the formula (XVI) is treated with a compound of the formula $ClCO_2R^7$, wherein $R^7$ is as defined above, via substantially the same procedure as described for Step (a) of Reaction Scheme 2 to form a compound of the formula (XVII).

In Step (d), a compound of the formula (XVII) is hydrolyzed via substantially the same procedure as described for Step (b) of Reaction Scheme 2 to form an amine of the formula (XVIII).

In Step (e), an amine of the formula (XVIII) is reacted with either $R^2OH$ and a coupling agent, or $R^2Cl$ and a base, via substantially the same procedures as described for Reaction Scheme 1, Step (e), to form a compound of the formula (Ic).

Starting ketones of the formula (II) and starting compounds of the formula (III) are known or can be prepared via known methods. Compounds of the formula $R^2OH$, $R^2Cl$ and $ClCO_2R^7$ are known and are either commercially available or can be prepared via established methods.

In the above processes, it is sometimes desirable and/or necessary to protect certain $R^1$, $R^2$, $R^3$ and $R^4$ etc., groups during the reactions. Conventional protecting groups are operable as described in Greene, et al, "Protective Groups In Organic Synthesis, 2nd Ed.", John Wiley & Sons, New York, (1991). For example, the groups listed in column 1 of Table 1 may be protected as indicated in column 2 of the table:

Other protecting groups well known in the art also may be used. After the reaction or reactions, the protecting groups may be removed by standard procedures.

Compounds useful in this invention are exemplified by the following preparative examples, which should not be construed to limit the scope of the present invention.

PREPARATION 1

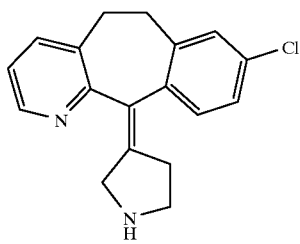

TABLE 1

PROTECTED GROUPS

| 1. GROUP TO BE PROTECTED | 2. PROTECTED GROUP |
|---|---|
| —COOH | —COOalkyl, —COObenzyl, —COOphenyl, 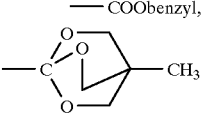 |
| >NH | >NCOalkyl, >NCObenzyl, >NCOphenyl |
| >CO |  |
| —OH | 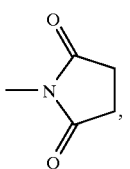, —OCH₂phenyl, —OCH₃, —OSi(CH₃)₂(t-Bu), |
| —NHR, wherein R is any substituent on an amino group within the scope of the claims | —N(R)—(tetrahydropyranyl), —NR—CO—CF₃, —NRCOCH₃, —NRCH₂phenyl |
| —NH₂ | —N(succinimidyl), —NH—C(O)—O(t-Bu) |

Step A:

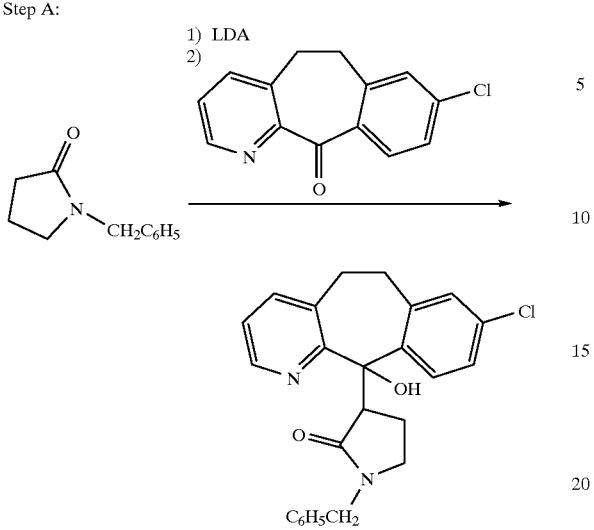

In a flame dried 2-neck flask combine THF (400 mL) and dry diisopropyl amine (0.135 mol, 13.74 g, 19.0 mL). Cool the solution to −78° C. and slowly add (dropwise) n-BuLi (2 M, 0.134 mol, 67 mL) over 5 min. Stir the resulting mixture at −78° C. for 45 min, then slowly add (dropwise) a THF solution of the lactam (0.123 mol, 21.6 g, 20 mL) over 5 min. Stir the reaction mixture at −78° C. for 1h, then raised to 0° C. for 1h, to give an opaque red solution. Cool the reaction mixture back down to −78° C. and add a THF solution of the ketone (0.123 mol, 30 g in 300 mL THF) via cannula. When the reaction is complete by TLC analysis (after about 2 hours), raise the temperature to −50° C. for 30 min, then add saturated NH4Cl (aqueous) to quench. Dilute the mixture with additional H2O and extract repeatedly with EtOAc. Combine the extracts and wash with brine. Dry the extracts over $Na_2SO4$, filter, and concentrate in vacuo to give a mixture of diastereomeric alcohols. Heat the mixture in EtOAc to give 19.9 g (42% yield) of the upper $R_f$ diastereomer as a solid. Chromatograph (silica gel, 2% $THF:CH_2Cl_2$ increasing gradually to 5% $THF:CH_2Cl_2$) the material obtained from the mother liquor to give 21.3 g (45% yield) of the lower $R_f$ diastereomer as a solid, and 2.9 g of unreacted ketone.

Analytical data for the upper $R_f$ diastereomer: MS (CI, M+H)=385, MP 164–166° C. Combustion Analysis Calc; C, 71.51; H, 5.76; N, 6.67; Cl, 8.44. Found: C, 71.55; H, 5.58; N, 6.67; Cl, 8.49.

Analytical data for the lower $R_f$ diastereomer: MS (CI, M+H)=385, Combustion Analysis Calc; C, 71.51; H, 5.76; N, 6.67; Cl, 8.44. Found: C, 71.46; H, 5.57; N, 6.66; Cl, 8.40.

Step B

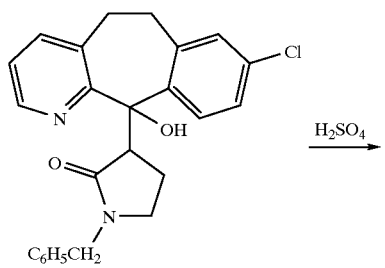

Combine 1.0 g (2.38 mmol) of the uuper $R_f$ diatereomer from Step A and concentrated $H_2SO_4$ at room temperature. Heat the mixture to 60° C. for 1.5 h, then cool to room temperature and poured into crushed ice. Basify the resulting solution to a pH of about 10 with 10% NaOH (aqueous) and extract repeatedly with $CH_2Cl_2$ (or EtOAc). Combine the extracts, wash the extracts with brine, then dry over $Na_2SO_4$, filtered and concentrate in vacuo to a residue. Chromatograph (silica gel, 5% acetone:$CH_2Cl_2$ increasing gradually to 5% MeOH:$CH_2Cl_2$) to give 200 mg of the E-N-benzyl isomer, and 600 mg of the Z-N-benzyl isomer as solids.

Analytical data for the E-N-benzyl isomer:: MS (CI, M+H)=401, MP 178–180.5 ° C. Combustion Analysis Calc; C, 74.90; H, 5.28; N, 699; Cl, 8.84. Found:

Analytical data for the Z-benzyl isomer: MS (CI, M+H) =401, Combustion Analysis Calc; C, 74.90; H, 5.28; N, 6.99; Cl, 8.84. Found: C, 74.78; H, 5.41; N, 6.97; Cl, 8.82.

Step C

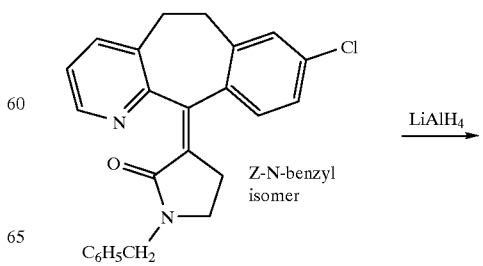

17

-continued

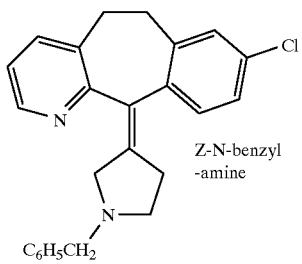

Z-N-benzyl-amine

Combine the Z-N-benzyl isomer from Step B and 5 mL of THF under a N₂ atmosphere. Cool the solution to 0° C., and add 70 mg of LiAlH₄ (1.867 mmol) in portions. Stir the mixture for about 30 min. at 0° C., then quench with EtOAc and MeOH. Filter through celite® to remove the aluminum salts, concentrate the filtrate and add 5% NaOH (aqueous). Extract the aqueous portion with EtOAc:THF (9:1), combine the organic phases and wash with brine. Dry over Na₂SO₄, filter and concentrate the filtrate in vacuo to a residue. Chromatograph (silica gel, 10% acetone:hexane increasing gradually to 20% acetone:hexane) to give 175 mg (51% yield) of the Z-N-benzylamine.

Analytical data for the Z-N-benzylamine: MS (CI, M+H) =387. high resolution MS Calc. for $C_{25}H_{24}N_2Cl$; 387.1628: Found; 387.1609.

Step D

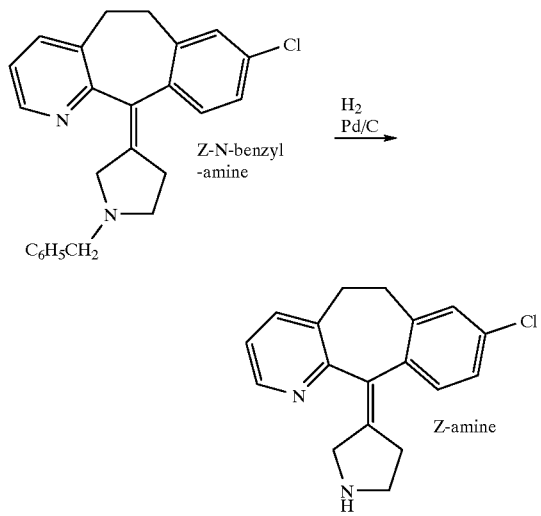

Z-N-benzyl-amine

Z-amine

Combine 500 mg of the Z-N-benzylamine from Step C (1.29 mmol), MeOH (20 mL), HOAc (5 mL), cyclohexadiene (5 mL) and 210 mg of 10% Pd/C under N₂ atmosphere. Carefully heat the mixture to 70° C. at which time hydrogen evolution began. After 1 hour and add hydrogen and continue heating at about 40° C. for an additional 1h. Filter the mixture through celite®, and concentrate the filtrate in vacuo to a residue. Add toluene and concentrate in vacuo again to remove residual HOAc. Chromatograph (silica gel, 5% MeOH:CH₂Cl₂ increasing gradually to 10% MeOH:CH₂Cl₂: 1% NH₄OH) to give 221 mg (58% yield) of the Z-amine product (P-1).

Analytical data for Z-amine: MS (CI, M+H)=296.

Using the starting ketone indicated and following substantially the same procedure as described in Preparation 1, the following amines were prepared:

18

| Starting Ketone | Amine |
|---|---|
| 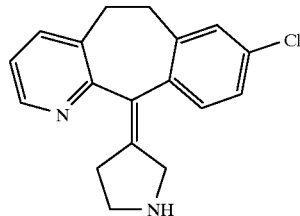 | (P-1A) |

PREPARATION 2

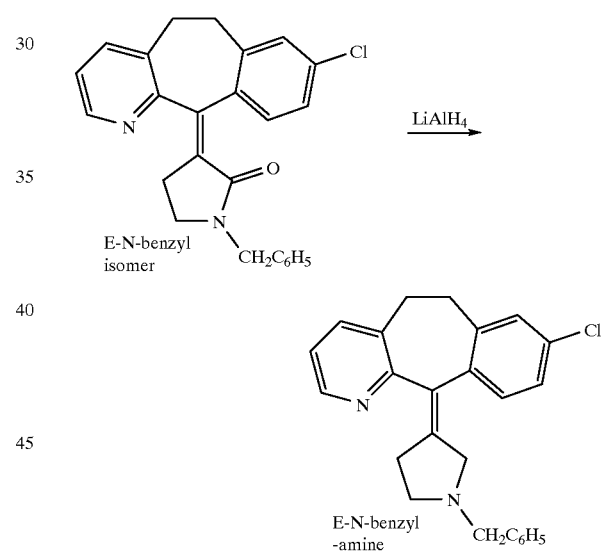

Step A

E-N-benzyl isomer

E-N-benzyl-amine

Combine 1.04 g of LiAlH₄ (27.7 mmol) and 75 mL of Et₂O under a N₂ atmosphere. Cool the mixture to 0° C., and add a THF solution of 2.20 g (5.49 mmol) of the E-N-benzyl isomer from Step B of Preparation 1, via syringe. After 120 min., quench the reaction mixture with EtOAc and MeOH, followed by the addition of 1% NaOH (aqueous). Extract the aqueous portion with EtOAc (4×75 mL), then with EtOAc:THF (4:1), and combine the extracts Wash the extracts with brine, dry over MgSO₄, filter and concentrate in vacuo to a residue. Chromatograph (silica gel, 15% acetone:EtOAc increasing gradually to 5% MeOH:EtOAc) to give 1.08 g (51% yield) of the E-N-benzylamine product.

Analytical data for the E-N-benzylamine: MS (CI, M+H) =387, Combustion Analysis Calc: C, 77.61; H, 5.99; N, 7.24; Cl, 9.16. Found: C, 77.80; H, 6.07; N, 7.20; Cl, 8.94.

Step B

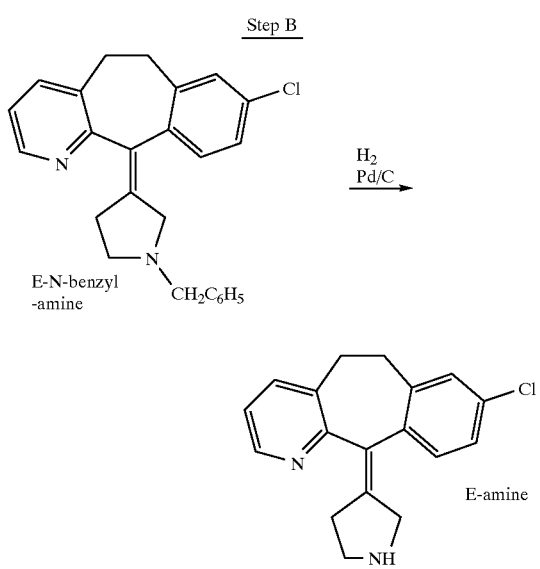

E-N-benzyl-amine

The E-N-benzylamine from Step A is hydrogenated using Pd/C via essentially the same procedure as described for the Z-isomer in Step D of Preparation 1 to give the E amine product Using the starting ketone indicated and following substantially the same procedure as described in Preparation 2, the following amines were prepared:

| Starting Ketone | Amine |
|---|---|
| 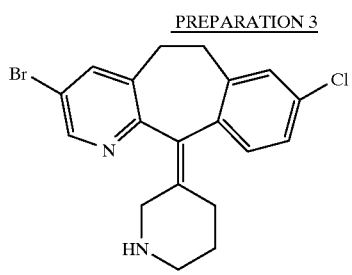 | (P-2A) |

PREPARATION 3

Step A:

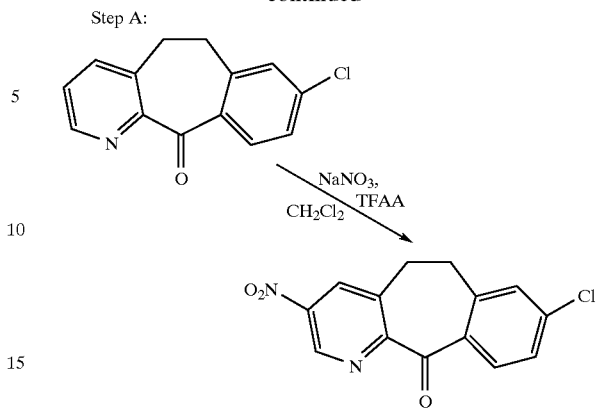

Combine 10 g (41.03 mmol) of the ketone and 100 mL of $CH_2Cl_2$ and cool to $-5°$ C. Add 7.0 mL (49.5 mmol) of TFAA, then add 3.7 g (43.53 mmol) $NaNO_3$ to the stirred mixture. Allow the mixture to warm to 20° C. and stir for 30 hours. Cool the mixture to 0° C. and slowly add a solution of 30 mL of concentrated $NH_4OH$ (aqueous) in 100 mL of water. Stir for 30 min. then add 300 mL of $CH_2Cl_2$ and 200 mL of water. Separate the layers and dry the organic phase over $MgSO_4$. Filter and concentrate in vacuo to a solid residue. Stir the solid in 100 mL of hot MeOH for 30 min. then allow the mixture to cool to room temperature. Filter, wash the solid with 20 mL of MeOH and dry under vacuum (0.2 mm Hg) at room temperature to give 4.9 g (41.4% yield) of the nitroketone product.

Step B:

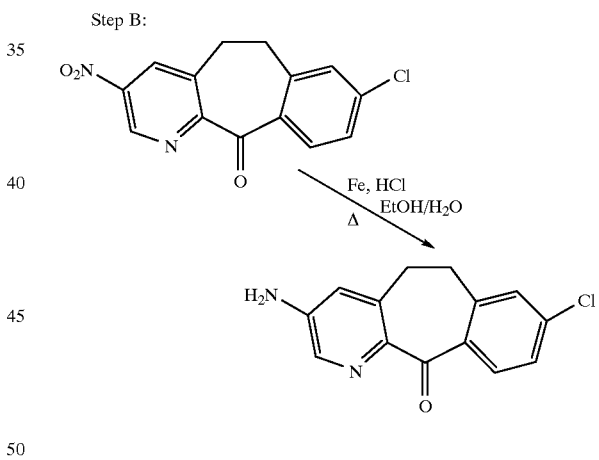

Combine 5 g (17.3 mmol) of the nitroketone from Step A, 140 mL of EtOH and 15 mL of water at room temperature, then add 3 g (54.5 mmol) of Fe powder. Add 1 mL of concentrated HCl and heat the mixture at reflux for 4 hours. Cool the mixture to room temperature and concentrate in vacuo to a volume of about 20 mL. Add 100 mL of water, 200 mL of $CH_2Cl_2$ and 30 mL of 20% NaOH (aqueous). Separate the layers and extract the aqueous phase with 200 mL of $CH_2Cl_2$. Combine the organic extracts, filter and wash with 100 mL of water. Dry over $MgSO_4$ then concentrate in vacuo to a residue. Stir the residue in a mixture of 20 mL of acetone and 100 mL $Et_2O$ to form a solid. Filter and wash the solid with 20 mL of $Et_2O$, then dry in vacuo at 20° C. to give 4.0 g (89.5% yield) of the aminoketone product.

Analytical data for the aminoketone: m.p.=199°–200° C.; MS (CI)=259, 261; Combustion analysis: calc. –C, 64.99; H, 4.28; N, 10.83, found –C, 64.79; H, 4.41; N, 10.58.

Step C:

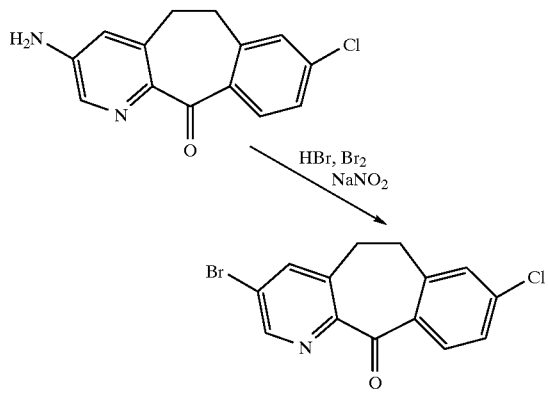

Combine 10 g (0.386 mole) of the aminoketone from Step B and 300 mL of 48% HBr at −5° C., then add 9.0 mL (1.74 mole) of Br$_2$ and stir at −5° C. for 20 min. Slowly add (dropwise) a solution of 10.5 g (1.52 mole) NaNO$_2$ in 25 mL of water, keeping the temperature at −5° C. Stir for 1 hour at −5° C., allow the mixture to warm to 20° C. over 1 hour and stir at 20° C. for 4 hours. Pour the mixture into 300 g of ice, and add 40% NaOH (aqueous) to the ice cold mixture to adjust to pH=14. Extract with CH$_2$Cl$_2$ (2×300 mL), combine the extracts and dry over MgSO$_4$. Filter and concentrate in vacuo to a residue. Chromatograph the residue (silica gel, 25% EtOAc/hexanes) to give 8.7 g (69.9% yield) of the bromoketone product.

Analytical data for the bromoketone: MS (CI)=322, 324.

Step D:

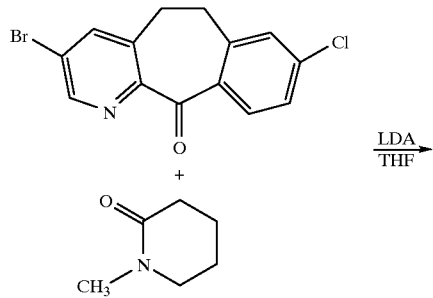

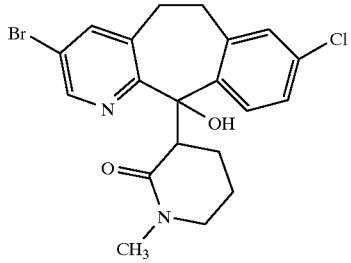

Slowly add (dropwise) 18 mL (45.0 mmol) of 2.5 M n-butyllithium in hexanes to a solution of 7.0 mL (49.41 mmol) diisopropylamine in 100 mL of THF at −78° C. Stir at −78° C. for 15 min. then add 7.0 mL (64 mmol) of N-methyl-2-piperidone. Stir the mixture at −78° C. for 30 min. then warm to −5° C. over a 1 hour period. Cool to −78° C. and slowly add (dropwise) a solution of 12 g (37.2 mmol) of the bromoketone from Step C in 200 mL of dry THF. Stir the mixture at −78° C. for 1 hour, then warm to −10° C. over 1.5 hours. Add 25 mL of water and concentrate in vacuo to remove about 200 mL of the solvent. Extract with 600 mL of CH$_2$Cl$_2$ and 300 mL of brine, and dry the organic extract over MgSO$_4$. Filter, concentrate in vacuo to a residue and stir the residue in a mixture of 30 mL of acetone and 20 mL of Et$_2$O to form a solid. Filter, wash the solid with 10 mL of Et$_2$O and dry at 20° C., 0.2 mm Hg, overnight to give 11.89 g of the product as a mixture of stereoisomers. Chromatograph (silica gel, 25% EtOAc/hexanes) the mother liquor and Et$_2$O wash to give an additional 1.0 g of the product (79.56% total yield).

Analytical data for the product of Step D: MS (CI, M+H)=437; combustion analysis: calc. —C, 55.12; H, 4.62; N, 6.43, found —C, 54.70; H, 4.57; N, 6.26.

Step E:

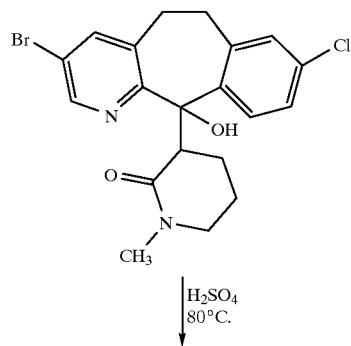

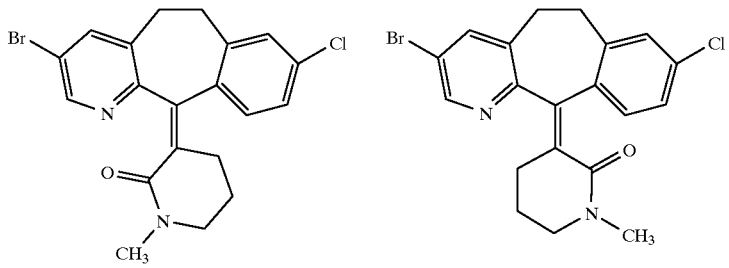

Combine 11.4 g (26.1 mmol) of the product from Step D and 100 mL of conentrated $H_2SO_4$ and heat to 80° C. for 4 hours. Cool the mixture to 20° C., pour into 300 g of ice and add 50% NaOH (aqueous) to the ice cold mixture to adjust to pH=14. Filter to collect the resulting solid, wash the solid wiith 300 mL of water, then dry at 20° C., 0.2 mm Hg, overnight. Chromatograph the solid (silica gel, 2% MeOH/EtOAc) to give 4.48 g of the Z-isomer and 4.68 g of the E-isomer of the product (total yield 84%)

Analytical data for Z-isomer: MS (CI, M+H)=417, 419; combustion analysis: calc. —C, 57.50; H, 4.34; N, 6.70, found —C, 57.99; H, 4.76; N, 6.66.

Analytical data for E-isomer: MS (CI, M+H)=417, 419; combustion analysis: calc. -C, 57.50; H, 4.34; N, 6.70, found —C, 57.23: H, 4.43; N, 6.65.

Step F:

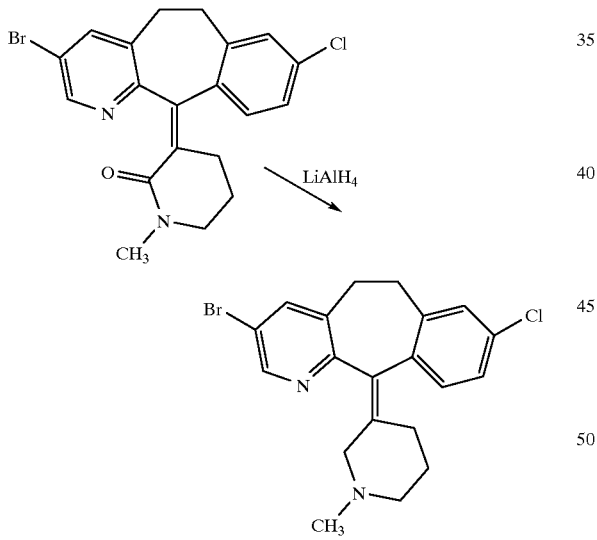

Combine 1.0 g (2.39 mmol) of the Z-isomer product from Step E and 10 mL of dry THF at -10° C. and add 110 mg (2.78 mmol) of $LiAlH_4$. Stir the mixture at -10° to -5° C. for 2 hours, then add 2 mL of EtOAc folowed by 20 mL of 10% potassium sodium tartrate tetrahydrate (aqueous), 5 mL of 10% NaOH (aqueous) and 150 mL of $CH_2Cl_2$. Separate the layers and dry the organic phase over $MgSO_4$. Filter and concentrate in vacuo to a residue. Chromatograph the residue (silica gel, first 25% EtOAc/hexanes, then 3% MeOH/EtOAc containing concentrated 1% $NH_4OH$) to give 480 mg (50% yield) of the Z-methylamine product.

Analytical data for the Z-methylamine: m.p.=160°–161° C.; MS (CI, M+H)=403, 405; combustion analysis:-calc. —C, 59.49; H, 4.99; N, 6.94, found —C, 59.75; H, 5.43; N, 6.79.

Step G:

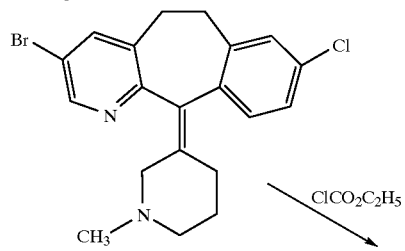

Combine 1.1 g (2.72 mmol) of the Z-methylamine from Step F and 20 mL o f toluene at 0° C. and add 1.0 mL (10.4 mmol) of $ClCO_2C_2H_5$. Add 1.0 mL (13.6 mmol) of EtkN and heat the mixture to 70° C. for 3 hours. Cool the mixture and concentrate in vacuo to a residue. Extract the residue with 50 mL of $CH_2Cl_2$ and wash the extract with 30 mL of water. Dry over $MgSO_4$, filter and concentrate in vacuo to a residue. Chromatograph the residue (silica gel, 20% EtOAc/hexanes) to give the crude product. Crystallize from a mixture of EtO and $CH_2Cl_2$ to give 510 mg (40.8% yield) of the Z-ethylcarbamate product.

Analytical data for the Z-ethylcarbamate: m.p.= 182°–183° C.; MS (CI, M+H)=461, 463; combustion analysis: calc. —C, 57.29; H, 4.80; N, 6.06, found —C, 57.38; H, 4.72; N, 6.08.

Step H:

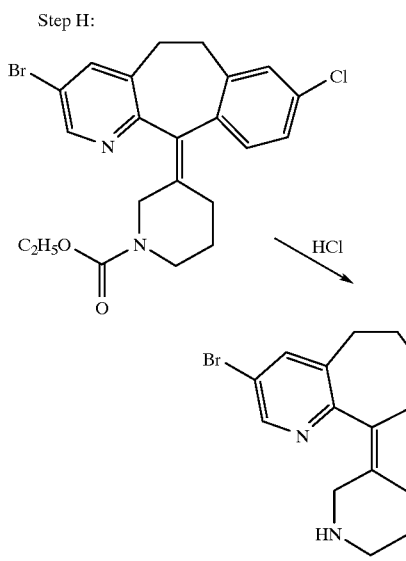

Combine 400 mg (0.866 mmol) of the Z-ethylcarbamate from Step G and 5 mL of concentrated HCl and heat at 100° C. overnight. Cool to 0° C. and slowly add :30% NaOH (aqueous) to basify the mixture. Extract with CH$_2$Cl$_2$ (2×250 mL) and dry the extract over MgSO$_4$. Filter and concentrate in vacuo to give 320 mg (94.86% yield) of the Z-amine product (P-3).

Analytical data for the Z-amine (P-3): MS (FAB, M+H)= 389, 391.

Using the starting ketone indicated and following substantially the same procedure as described in Steps D to H of Preparation 3, the following amines were prepared:

| Starting Ketone | Amine |
|---|---|
| 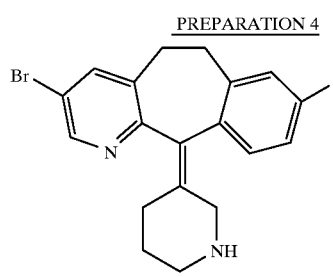 | (P-3A), m.p. = 169°–170° C. |

PREPARATION 4

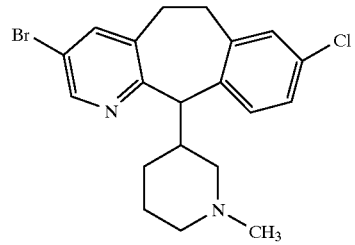

Step A:

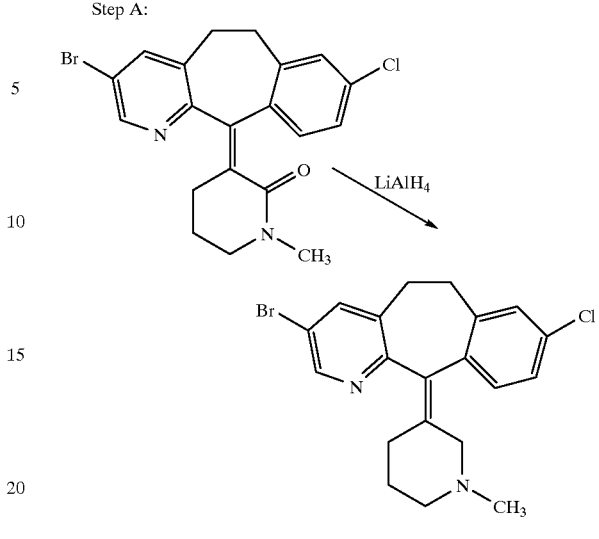

Combine 3.4 g (8.15 mmol) of the E-isomer product from Step E of Preparation 3 and 40 mL of dry THF at −5° C. and add 470 mg (11.9 mmol) of LiAlH$_4$. Stir the mixture at 0° C. for 5 hours, then add 5 mL of water, 20 mL of 10% potassium sodium t-artrate tetrahydrate (aqueous), 5 mL of 10% NaOH (aqueous) and 150 mL of CH$_2$Cl$_2$. Separate the layers and dry the organic phase over MgSO$_4$. Filter and concentrate in vacuo to a residue. The residue is a mixture of the product compound and a compound of the formula

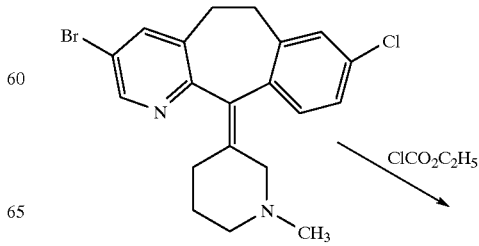

Chromatograph the residue (silica gel, 2% MeOH/EtOAc) to give 1.3 g (40% yield) of the E-methylamine product.

Analytical data for the E-methylamine: m.p.=140°–141° C.; MS (CI, M+H)=403, 405; combustion analysis: calc. —C, 5 59.49; H, 4.99; N, 6.94, found —C, 59.11; H, 4.75; N, 6.98.

Step B:

27
-continued

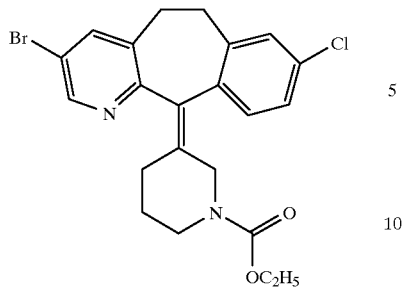

Using 0.4 g (0.99 mmol) of the E-methylamine from Step A, 15 mL of toluene, 0.5 mL (5.2 mmol) of ClCO$_2$C$_2$H$_5$, and 0.5 mL (6.8 mmol) of Et$_3$N, and substantially the same procedure as described in Preparation 3, Step G, 230 mg (51.1% yield) of the E-ethylcarbamate product is prepared.

Analytical data for the E-ethylcarbamate: m.p.= 186°–187° C.; MS (CI, M+H)=463, 464; combustion analysis: calc. —C, 57.29; H, 4.80; N, 6.06, found —C, 57.43; H, 5.11; N, 6.09.

Step C:

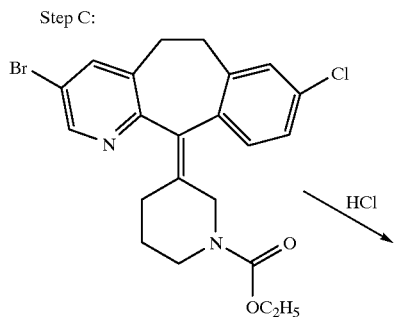

HCl

28
-continued

The E-ethylcarbamate from Step B is converted to the E-amine (P-4) in 97.8% yield using substantially the same procedure as described in Preparation 3, Step H.

Analytical data for the E-amine (P-4): m.p.=166°–167° C.; MS (CI)=389, 391; combustion analysis: calc. —C, 57.88; H, 4.66; N, 7.10, found —C, 57.63; H, 4.61; N, 7.03.

Using the starting ketone indicated to prepare the appropriate E-isomer via the procedures described in Steps D and E of Preparation 3, Steps A-E; the following amines were prepared via substantially the same procedure as described in Steps A-C of Preparation 4:

| Starting Ketone | Amine |
|---|---|
| 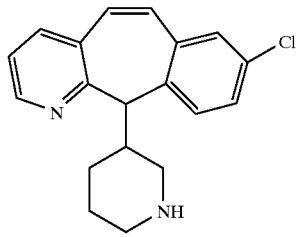 | (P-4A), m.p. = 140°–141° C. |

PREPARATION 5

Step A:

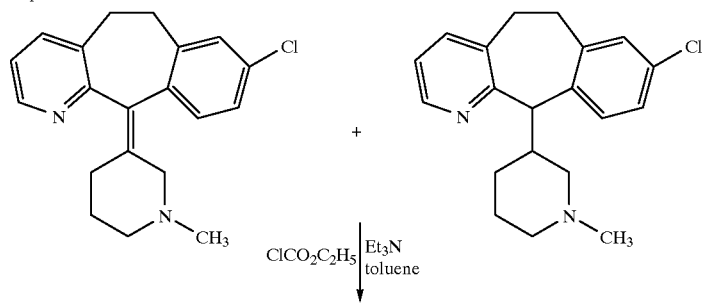

ClCO$_2$C$_2$H$_5$ | Et$_3$N toluene

-continued

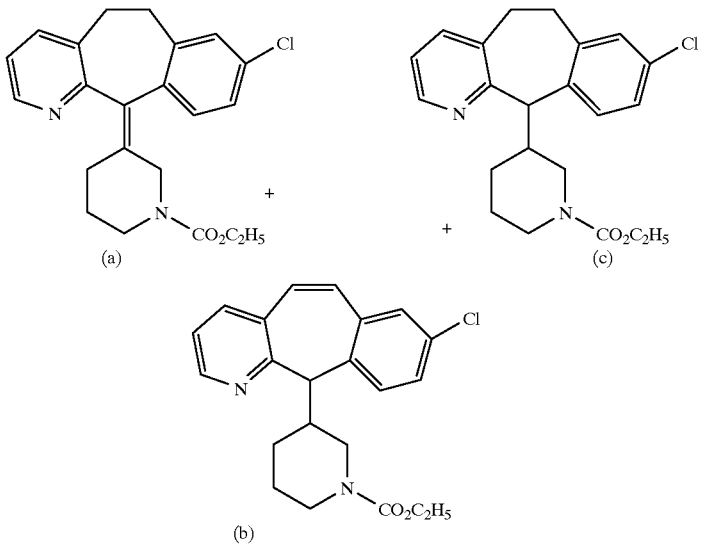

(a) + (c) +

(b)

Combine 20 g (61.5 mmol) of the crude (no chromatography) E-methyl-amine obtained from Preparation 4, Step A (using the appropriate starting ketone), and 200 mL of toluene at 0° C., and add 20 mL (208 mmol) of $ClCO_2C_2H_5$. Add 20 mL (272 mmol) of $Et_3N$, then heat to 80° C. and stir for 4 hours. Cool to room temperature and concentrate in vacuo to a residue. Extract the residue with 300 mL of $CH_2Cl_2$, wash the extract with 200 mL of water, then dry over $MgSO_4$. Filter, concentrate in vacuo to a residue, then chromatograph the residue (silica gel, 70% EtOAc/hexanes) to give 5.0 g of product (a), 4.2 g of product (b), and 300 mg of product (c).

Analytical data for product (a): MS (CI, M+H)=383.
Analytical data for product (b): MS (CI, M+H)=383.
Analytical data for product (c): MS (CI, M+H)=385.

Step B:

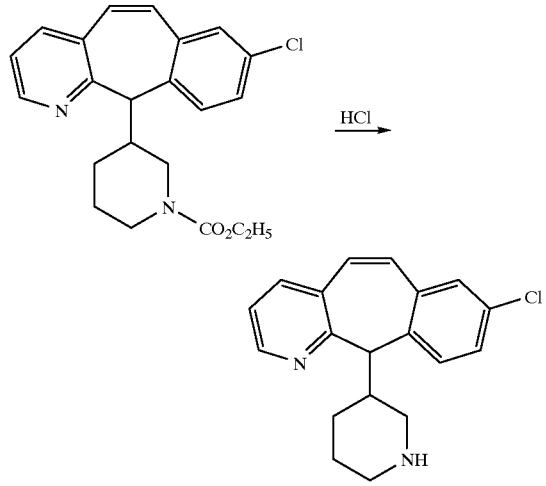

Combine 4.0 g (10.4 mmol) of product (b) from Step A and 20 mL of concentrated HCl and heat at 80° C. overnight. Cool to 20° C., basify to pH=14 with 20% NaOH (aqueous), and extract with 200 mL of $CH_2Cl_2$. Wash the extract with 25 ml, of water, dry over $MgSO_4$, filter and concentrate in vacuo to a residue. Chromatograph the residue (silica gel, 10% MeOH/EtOAc+2% $NH_4OH$ (aqueous)), then triturate with 15 mL of acetone/Et2O to give 1.96 g (60.5% yield) of the amine product (P-5).

Analytical data for amine (P-5): m.p.=157°–158° C.; MS (CI, M+H)=311, 313.

PREPARATION 6

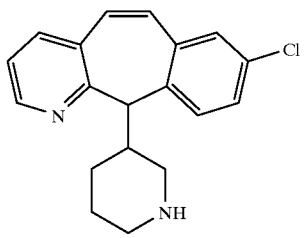

Combine 400 mg (1.03 mmol) of product (c) from Preparation 5, Step A, and 5 mL of EtOH at 20° C., then add a solution of 0.23 g (4.15 mmol) KOH in 10 mL of water. Heat the mixture at reflux for 3 days, cool to room temperature and concentrate in vacuo to a residue. Extract the residue with 80 mL of $CH_2Cl_2$ and wash the extract with 50 mL of water. Dry over $MgSO_4$, filter and concentrate in vacuo to a residue. Chromatograph the residue (silica gel, 10% MeOH/EtOAc+2% $NH_4OH$ (aqueous), then triturate with 10 mL of $Et_2O$ to give 200 mg (61.5% yield) of the amine (P-6).

Analytical data for the amine (P-6): MS (CI, M+H)=313, 315

PREPARATION 7

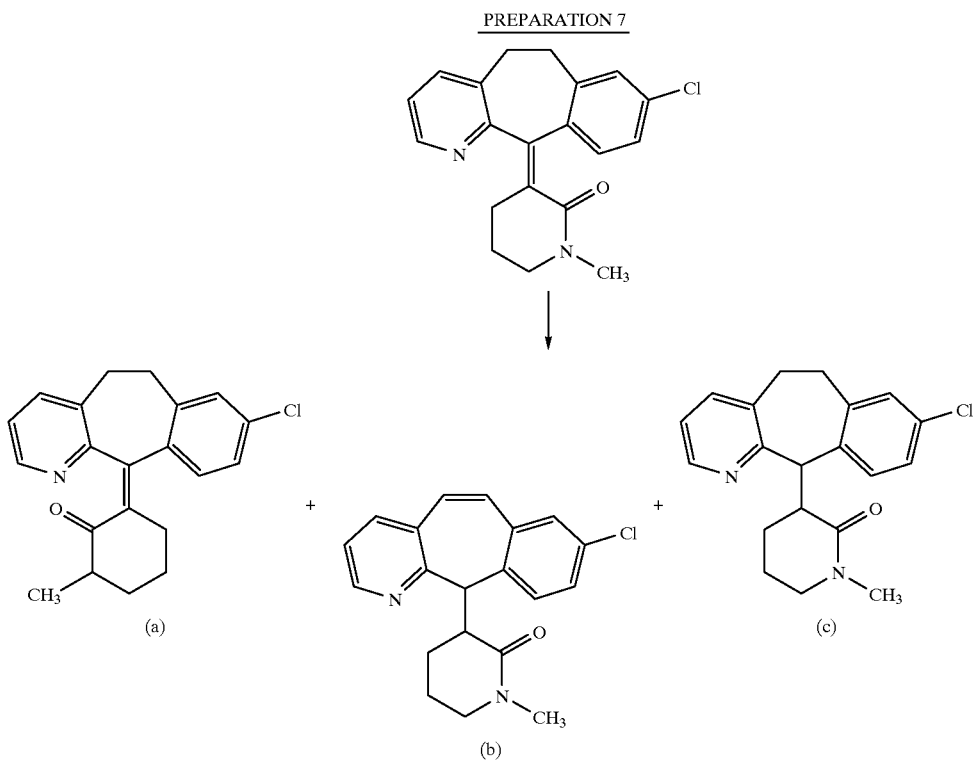

Combine 1.0 g (2.95 mmol) of E-isomer product (obtained using the appropriate ketone) from Preparation 3, Step E, 30 mL of glacial HOAc and 1.0 g (15.29 mmol) of Zn powder and heat the mixture at 100° C. overnight. Filter through celite®, wash the filter cake with 20 mL of galcial HOAc, then concentrate the filtrate in vacuo to a residue. Basify the residue with 15 mL of concentrated $NH_4OH$ (aqueous), add 50 mL of water and extract with $CH_2Cl_2$ (2×100 mL). Dry the combined extracts over $MgSO_4$, filter and concentrate in vacuo to a residue. Chromatograph the residue (silica gel, 5% MeOH/EtOAc+2% concentrated $NH_4OH$ (aqueous)) to give three products: 300 mg (30% yield) of the product (a); 250 mg (25% yield) of the product (b); and 250 mg (25% yield) of the product (c).

Analytical data for product (c): m.p.=172°–173° C., MS (CI, M+H)=340, 342.

Analytical data for product (b): m.p.=142°–144° C., MS (CI, M+H)=339, 341.

EXAMPLE 1

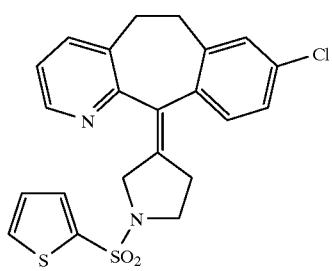

Combine 115 mg of the Z-amine product (P-1) from Preparation 1 (0.389 mmol), 5 mL of pyridine (5 mL) and a catalytic amount (15 mg) of DMAP under a $N_2$ atmosphere. Cool the solution to 0° C. and add 175 mg of 2-thienylsufonyl chloride (0.961 mmol). Stir for 10 min. at 0° C., then warm to room temperature and stir for 17 hours. Quench the reaction mixture by the adding a solution of $NaHCO_3$ (aqueous), and extract the aqueous layer with EtOAc-THF (20:1). Combine the extracts, wash with brine, dry over $Na_2SO_4$, filter and concentrate in vacuo to a residue. Chromatograph (silica gel, 25% EtOAc:hexane increasing gradually to 35% EtOAc:hexane) to give 65 mg (39% yield) of the Z-N-(2-thienyl)sulfonamide product (E-1).

Analytical data for the Z-N-(2-thienyl)sulfonamide: MS (CI, M+H)=443.

Using the appropriate sulfonyl chloride and the amine indicated, and following substantially the same procedure as described for Example 1, the following sulfonamide compounds were prepared:

| Amine | Amide | Analytical Data |
|---|---|---|
| P-2A | 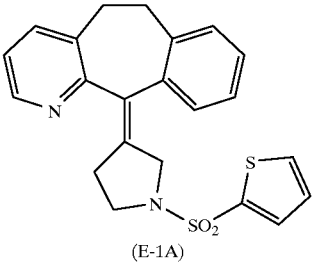 (E-1A) | MS (FAB, M + H) = 443 |
| P-1A | 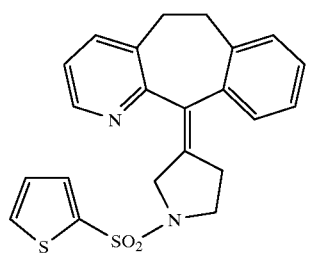 (E-1B) | MS (CI, M + H) = 409 |
| P-3 | 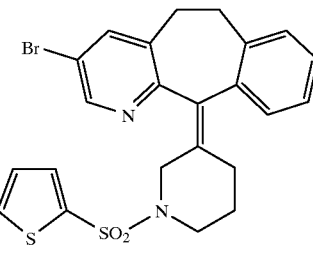 (E-1C) | m.p. = 165°–167° C. MS (CI, M + H) = 569, 571 |
| P-3 | 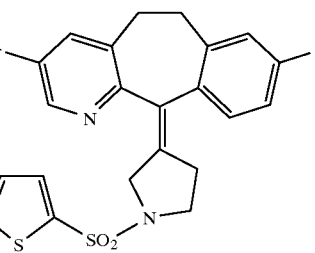 (E-1D) | m.p. = 183°–184° C. MS (CI, M + H) = 535, 537 |
| P-3 | 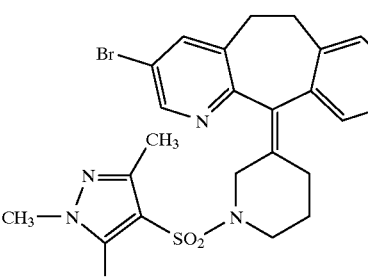 (E-1E) | m.p. = 251°–252° C. MS (CI) = 583, 585 |

-continued
| Amine | Amide | Analytical Data |
|---|---|---|
| P-4 | 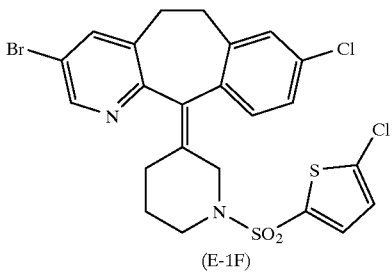 (E-1F) | m.p. = 171°–172° C. MS (CI) 569, 571 |
| P-3A | 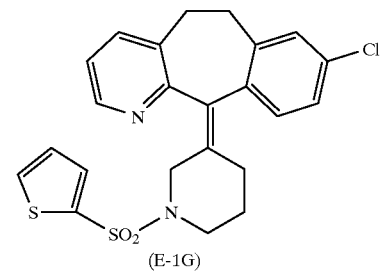 (E-1G) | MS (CI, M + H) = 457, 459 |
| P-3A | 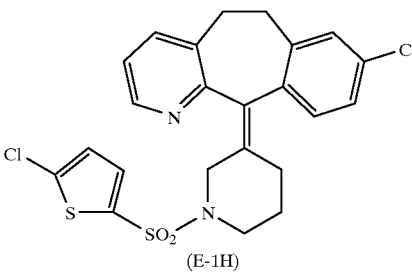 (E-1H) | m.p. = 154°–155° C. MS (CI) = 452, 454 |
| P-4A | 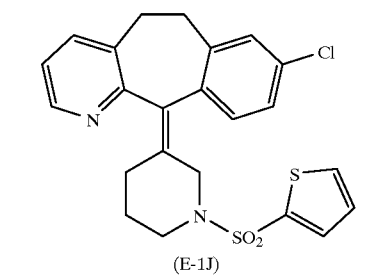 (E-1J) | m.p. = 254–255° C. MS (CI, M + H) = 457, 459 |
| P-4A | 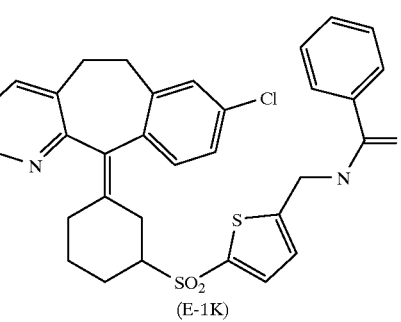 (E-1K) | MS (CI, M + H) = 590, 592 |

-continued

| Amine | Amide | Analytical Data |
|---|---|---|
| P-3A | (E-1M) | m.p. = 134°–136° C.<br>MS (CI, M + H) = 515, 517 |
| P-3A | (E-1N) | m.p. = 220° C. (dec.)<br>MS (FAB, M + H) = 501, 503 |

EXAMPLE 2

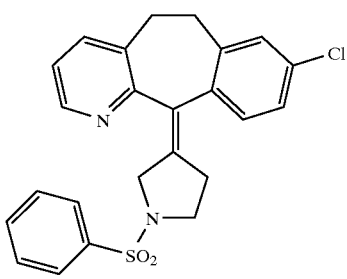

Combine 110 mg of the Z-amine product (P-1) from Preparation 1 (0.339 mmol), 5 mL of pyridine and a catalytic amount (10 mg) of DMAP under a $N_2$ atmosphere. Cool the solution to 0° C. and add $C_6H_5SO_2Cl$ (1.17 mmol, 207 mg). Stir the mixture for 10 min at 0° C., then warm to room temperature and stir for 17h. Add a solution of $NaHCO_3$ (aqueous) to quench the reaction mixture, then extract the aqueous layer with EtOAc-THF (20:1). Combine the extracts, wash with brine, dry over $Na_2SO_4$, a filter and concentrate in vacuo to a residue. Chromatograph (silica gel, 25% EtOAc:hexane increasing gradually to 35% EtOAc:hexane) to give 80 mg (54% yield) of the Z-benzenesulfonamide product (E-2).

Analytical data for the Z-N-benzenesulfonamide: MS (CI, M+H)=437.

Using the appropriate sulfonyl chloride and the amine indicated, and following substantially the same procedure as described for Example 2, the following sulfonamide compounds were prepared:

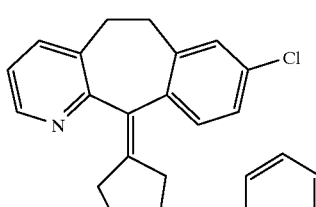

| Amine | Amide | Analytical Data |
|---|---|---|
| P-2 | (E-2A) | MS (FAB, M + H) = 437 |

| Amine | Amide | Analytical Data |
|---|---|---|
| P-2A | (E-2B) | |
| P-1A | (E-2C) | MS (CI, M + H) = 403 |
| P-3 | (E-2D) | m.p. = 184°–185° C.<br>MS (CI, M + H) = 529, 531 |
| P-3A | (E-2E) | MS (CI) = 451, 453 |
| P-3A | (E-2F) | m.p. = 178°–179° C.<br>MS (CI, M + H) = 496 |

| Amine | Amide | Analytical Data |
|---|---|---|
| P-3A | 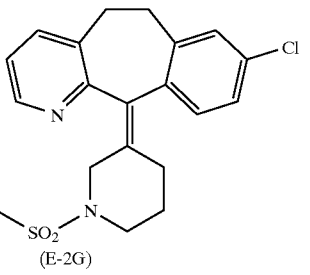 (E-2G) | m.p. = 160°–161° C. MS (CI) = 481, 483 |
| P-3A | 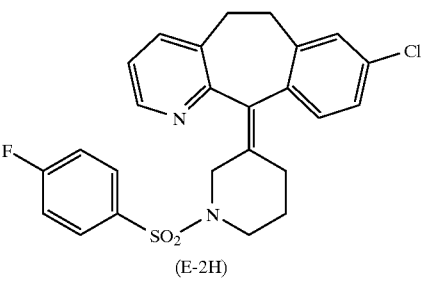 (E-2H) | m.p. = 173°–174° C. MS (CI, M + H) = 469, 471 |
| P-3A | 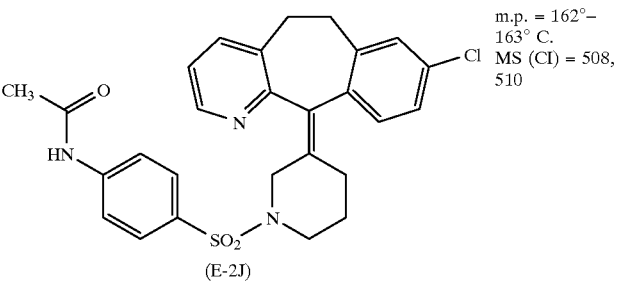 (E-2J) | m.p. = 162°–163° C. MS (CI) = 508, 510 |
| P-3A | 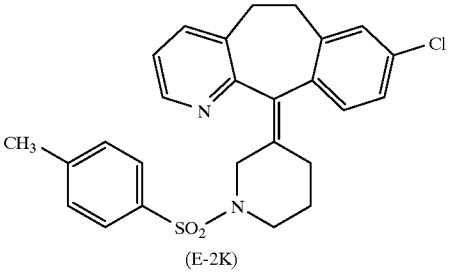 (E-2K) | MS (CI) = 465, 467 |
| P-3A | 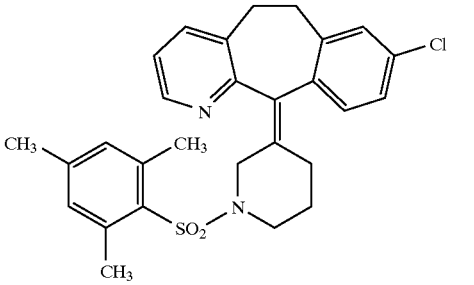 (E-2L) | m.p. = 227°–229° C. MS (CI) = 493, 495 |

-continued
| Amine | Amide | Analytical Data |
|---|---|---|
| P-3A | 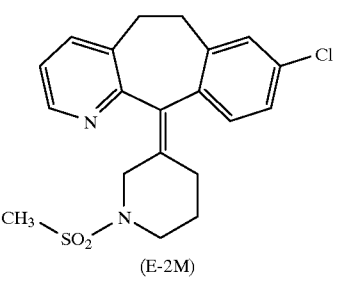 (E-2M) | m.p. = 189°–190° C.<br>MS (CI, MH) = 389, 391 |
| P-3A | (E-2N) | m.p. = 198°–199° C.<br>MS (CI) = 465, 467 |
| P-4A | (E-2P) | m.p. = 235°–236° C.<br>MS (CI, M + H) = 451, 453 |
| P-4A | (E-2Q) | m.p. = 232°–233° C.<br>MS (CI, M + H) = 496, 498 |
| P-4A | (E-2R) | m.p. = 168°–169° C.<br>MS (CI, M + H) = 481, 483 |

-continued

| Amine | Amide | Analytical Data |
|---|---|---|
| P-4A | 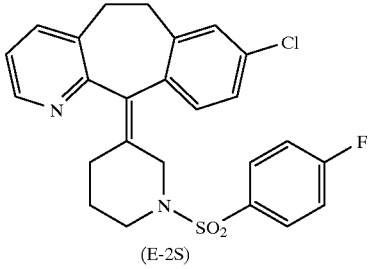 (E-2S) | m.p. = 154°–155° C.<br>MS (CI, M + H) = 469, 471 |
| P-4A | 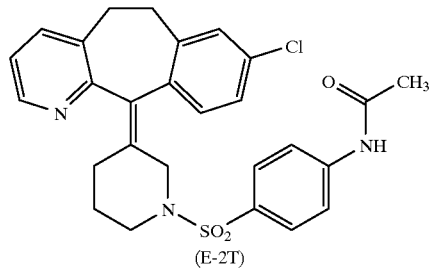 (E-2T) | m.p. = 147°–149° C.<br>MS (CI, M + H) = 508, 510 |
| P-5 | 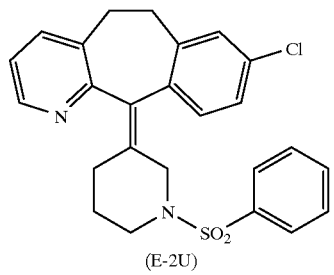 (E-2U) | m.p. = 178°–179° C.<br>MS (FAB, M + H) = 451, 453 |
| P-5 | 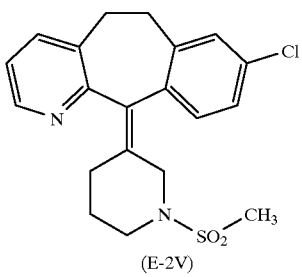 (E-2V) | M.P. = 231°–232° C.<br>MS (CI, M + H) = 389, 391 |

EXAMPLE 3

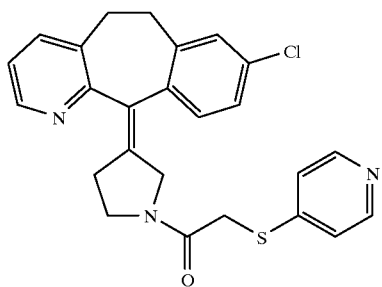

Combine 80 mg of the E-amine product (P-2) from Preparation 2 (0.270 mmol) 3 mL of DMF and 2 mL of NMM under a $N_2$ atmosphere. Cool the mixture to 0° C. and add 110 mg of HOBT (0.888 mmol), 250 mg of DEC (1.31 mmol), and 0.651 mmol of (4-pyridylthio)acetic acid. After 30 min., warm to room temperature and stir for 24 hours. Concentrate in vacuo to a residue, dilute the residue with $NaHCO_3$ (aqueous), and extract with $CH_2Cl_2$. Combine the extracts, wash with brine, dry over $Na_2SO_4$, filter and concentrate in vacuo to give a residue. Decolorize with activated carbon and chromatograph (silica gel, 5% $MeOH:CH_2Cl_2$ increasing gradually to 10% $MeOH:CH_2Cl_2$) to give 45 mg (37% yield) of the E-(4-pyridylthio)amide product (E-3).

Analytical data for the E-(4-pyridylthio)amide: MS (CI, M+H)=448.

Using the appropriate carbocylic acid and the amine indicated, and following substantially the same procedure as described for Example 3, the following amide compounds were prepared:

| Amine | Amide | Analytical Data |
|---|---|---|
| P-2 | 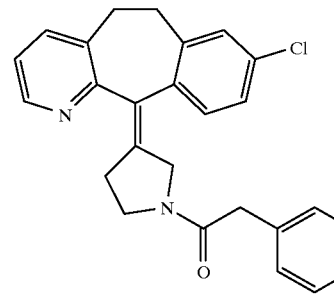<br>(E-3A) | MS (CI, M + H) = 415 |
| P-2 | 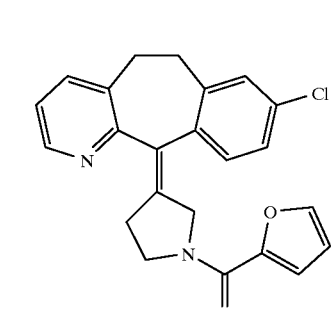<br>(E-3B) | MS (CI, M + H) = 391 |
| P-6 | 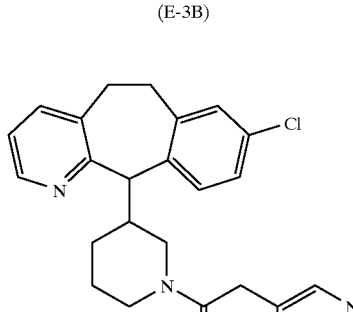<br>(E-3C) | MS (CI, M + H) = 432, 434 |
| P-6 | 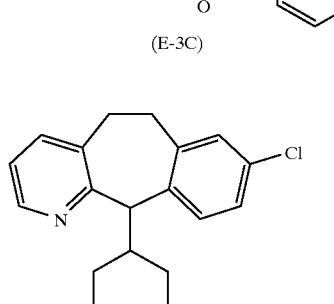<br>(E-3D) | MS (CI, M + H) = 432, 434 |

| Amine | Amide | Analytical Data |
|---|---|---|
| P-3A | 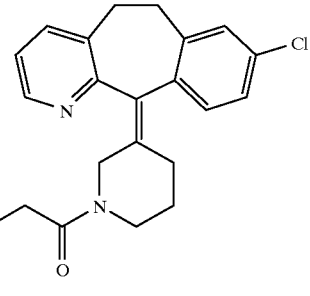<br>(E-3E) | MS (CI, M + H) = 430, 432 |
| P-3A | 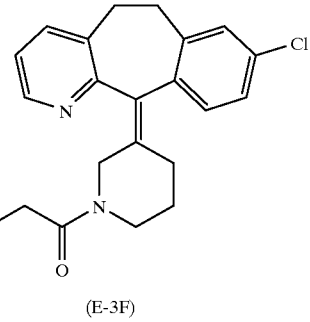<br>(E-3F) | MS (CI, M + H) = 430, 432 |
| P-3A | 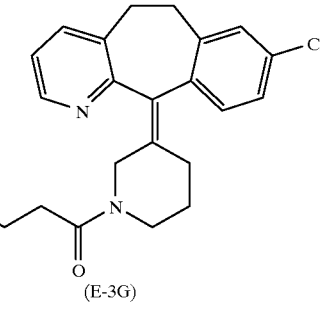<br>(E-3G) | MS (CI, M + H) = 443, 445 |
| P-4A | 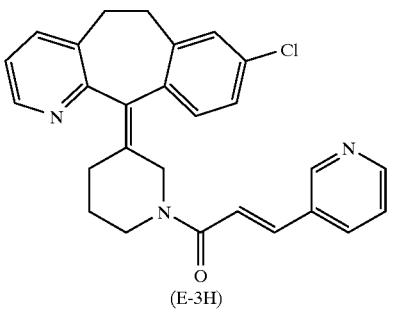<br>(E-3H) | m.p. = 165°–166° C.<br>MS (CI, M + H) = 442, 444 |

| Amine | Amide | Analytical Data |
|---|---|---|
| P-4A | 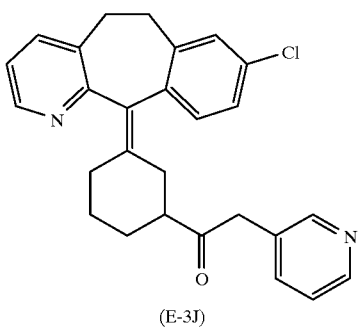<br>(E-3J) | m.p. = 157°–158° C.<br>MS (CI, M + H) = 430, 432 |
| P-4A | 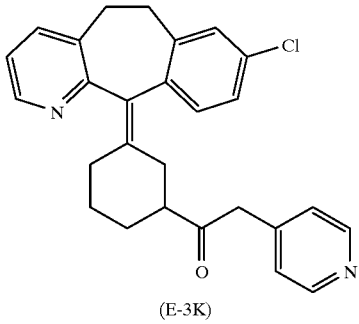<br>(E-3K) | MS (CI, M + H) = 430, 432 |
| P-4A | 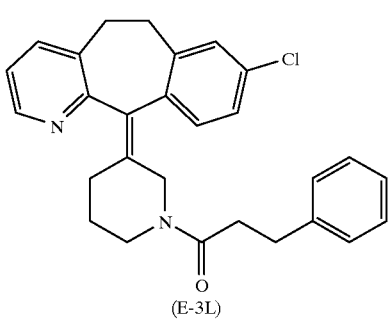<br>(E-3L) | MS (CI, M + H) = 443, 445 |
| P-1 | 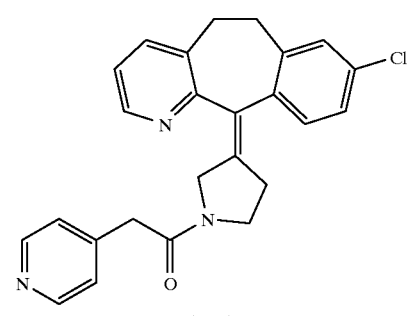<br>(E-M) | MS (CI, M + H) = 416 |

-continued

| Amine | Amide | Analytical Data |
|---|---|---|
| P-1 | 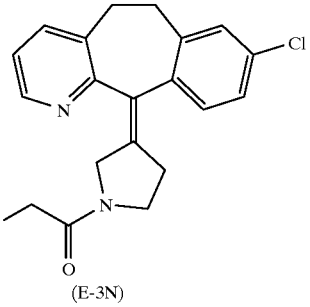(E-3N) | MS (CI, M + H) = 448 |

EXAMPLE 4

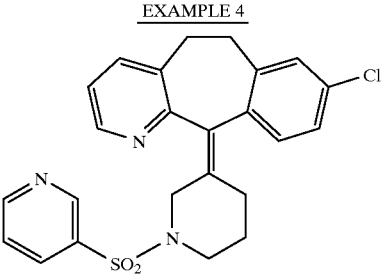

Combine 100 mg (0.626 mmol) of 3-pyridinesulfonic acid and 3 mL of anhydrous pyridine at 0° C. and add 100 mg (0.406 mmol) pf 4-nitrobenzenesulfonyl chloride. Add 5 mg of DMAP and stir the mixture at 0° C. for 7 hours. Add 80 mg (0.258 mmol) of the Z-amine (P-3A) from Preparation 3 and stir the mixture for 1 hour at 0° C., then overnight at 20° C. Add 50 mL of CH$_2$Cl$_2$ and 20 mL of water, separate the layers, and wash the organic phase with water. Dry over MgSO$_4$, filter and concentrate in vacuo to a residue. Chromatograph the residue (silica gel, 5% MeOH/EtOAc+1% concentrated NH$_4$OH (aqueous)), crystallize from 10 mL of Et$_2$O and dry the resulting solid at 60° C. in vacuo to give 180 mg (68.9% yield) of the Z-3-pyridylsulfonamide product (E-4).

Analytical data for the Z-3-pyridylsulfonamide (E-4): m.p.=158°–159° C., MS (CI)=452, 454.

Using the the E- or Z-amine indicated, and following substantially the same procedure as described for Example 4, the following sulfonamide compounds were prepared:

| Amine | Amide | Analytical Data |
|---|---|---|
| P-5 | 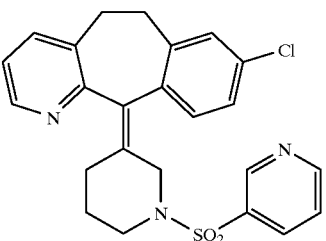(E-4A) | m.p. = 178°–179° C. MS (CI, M + H) = 452, 454 |

-continued

| Amine | Amide | Analytical Data |
|---|---|---|
| P-4A | 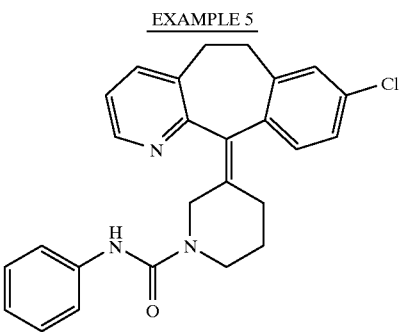(E-4B) | m.p. = 214°–215° C. MS (CI, M + H) = 452, 454 |

EXAMPLE 5

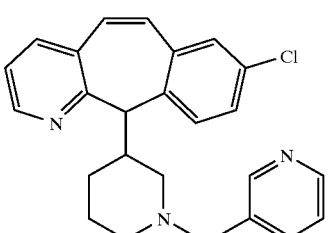

Combine 70 mg (0.225 mmol) of Z-amine (P-3A) from Preparation 3, 0.2 mL (1.53 mmol) of C$_6$H$_5$N=C=O and 15 mL of CH$_2$Cl$_2$ at 0° C., add 0.2 mL (2.72 mmol) of Et$_3$N and stir at 20° C. overnight. Add 20 mL of water and 25 mL of CH$_2$Cl$_2$, separate the layers and dry the organic phase over MgSO$_4$. Filter, concentrate in vacuo to a residue, chromatograph the residue (silica gel, 20% EtOAc/hexanes) and crystallize from 10 mL of Et$_2$O. Dry the resulting solid in vacuo at 20° C. to give 75 mg (78% yield) of the Z-phenylurea product (E-5).

Analytical data for the Z-phenylurea (E-5): m.p.= 184°–185° C.; MS (CI, M+H)=430, 432.

EXAMPLE 6

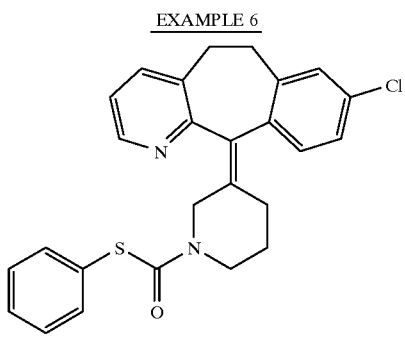

Combine 25 mg (0.08 mmol) of the Z-amine (P-3A) from Preparation 3, 0.2 mL (2.72 mmol) of $Et_3N$ and 2 mL of anhydrous pyridine at 0° C. and add 0.2 g (1.13 mmol) of phenyl chlorothioformate. Add 5 mg (0.04 mmol) of DMAP and stir the mixture overnight. Concentrate in vacuo to a residue and partition the residue between 25 mL of EtOAc and 20 mL of water. Dry the organic phase over $Na_2SO_4$, filter and concentrate in vacuo to a residue. Chromatograph the residue (silica gel, 5% MeOH/EtOAc), triturate with hexanes and dry the resulting solid at 20° C. in vacuo to give 30 mg (83.6% yield) of the Z-phenylthio-carbamate product (E-6).

Analytical data for the Z-phenylthiocarbamate (E-6): m.p.=187°–188° C.; MS (CI)=447.

EXAMPLE 7

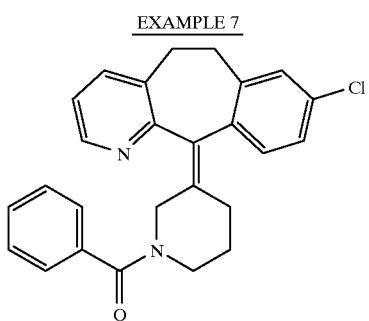

Combine 40 mg (0.129 mmol) of the Z-amine (P-3A) from Preparation 3, 0.5 mL (0.391 mmol) of benzoyl chloride and 5 mL of anhydrous pyridine at 0° C., add 2 mg of DMAP, then stir the mixture overnight at 20° C. Add 20 mL of $CH_2Cl_2$ and 10 mL of water, separate the layers and wash the organic phase with 20 mL of brine. Dry the organic phase over $MgSO_4$, filter and concentrate in vacuo to a residue. Chromatograph the residue (silica gel, 5% MeOH/EtOAc+ 1% concentrated $NH_4OH$ (aqueous)), recrystallize the resulting solid from acetone/hexanes and dry the at 60° C. in vacuo to give the Z-phenylamide product (E-7).

Analytical data for the Z-phenylamide (E-7): m.p.= 215°–216° C.; MS (CI, M+H)=415, 417.

Using the appropriate acid chloride and the E- or Z-amine indicated, and following substantially the same procedure as described for Example 7, the following amide compounds were prepared:

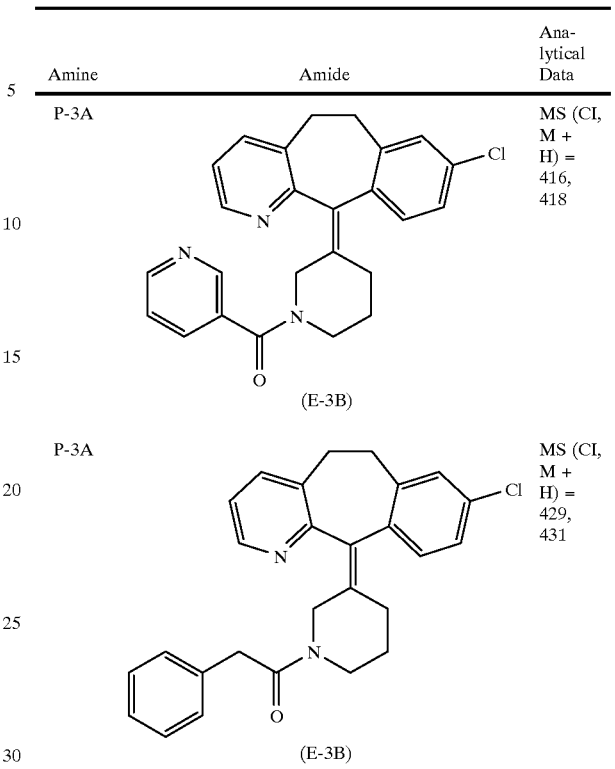

| Amine | Amide | Analytical Data |
|---|---|---|
| P-3A | (E-3B) | MS (CI, M + H) = 416, 418 |
| P-3A | (E-3B) | MS (CI, M + H) = 429, 431 |

Assays

1. In vitro enzyme assays: Inhibition of farnesyl protein transferase and geranylgeranyl protein transferase.

Both farnesyl protein transferase (FLT) and geranylgeranyl protein transferase (GGPT) I were partially purified from rat brain by ammonium sulfate fractionation followed by Q-Sepharose (Pharmacia, Inc.) anion exchange chromatography essentially as described by Yokoyama et al (Yokoyama, K., et al., (1991), A protein geranylgeranyl transferase from bovine brain: Implications for protein prenylation specificity, Proc. Natl. Acad. Sci USA 88: 5302–5306, the disclosure of which is incorporated herein by reference thereto). Human farnesyl protein transferase was also expressed in $E.\ coli$, using cDNA clones encoding both the a and b subunits. The methods used were similar to those published (Omer, C. et al., (1993), Characterization of recombinant human farnesyl protein transferase: Cloning, expression, farnesyl diphosphate binding, and functional homology with yeast prenylprotein transferases, Biochemistry 32: 5167–5176). Human farnesyl protein transferase was partially-purified from the soluble protein fraction of $E.\ coli$ as described above, the tricyclic farnesyl protein transferase inhibitors disclosed herein inhibited both human and rat enzyme with similar potencies. Two forms of $val^{12}$-Ha-Ras protein were prepared as substrates for these enzymes, differing in their carboxy terminal sequence. One form terminated in cysteine-valine-leucine-serine (Ras-CVLS) the other in cystein-valine-leucine-leucine (Ras-CVLL). Ras-CVLS is a substrate for the farnesyl protein transferase while Ras-CVLL is a substrate for geranylgeranyl protein transferase I. The cDNAs encoding these proteins were constructed so that the proteins contain an amino-terminal extension of 6 histidine residues. Both proteins were expressed in $Escherichia\ coli$ and purified using metal chelate affinity chromatography. The radiolabelled isoprenyl pyrophosphate substrates, [$^3H$]farnesyl pyrophosphate and

[³H]geranylgeranyl pyrophosphate, were purchased from DuPont/New England Nuclear.

Several methods for measuring farnesyl protein transferase activity have been described (Reiss et al 1990, Cell 62: 81; Schaber et al 1990, J. Biol. Chem. 265: 14701; Manne et al 1990, PNAS 87: 7541; and Barbacid & Manne 1993, U.S. Pat. No. 5,185,248). The activity was assayed by measuring the transfer of [³H]farnesyl from [³H]farnesyl pyrophosphate to Ras-CVLS using conditions similar to those described by Reiss et al. 1990 (Cell 62: 81) The reaction mixture contained 40 mM Hepes, pH 7.5; 20 mM magnesium chloride; 5 mM dithiothreitol; 0.25 µM [³H] farnesyl pyrophosphate; 10 ml Q-Sepharose-purified farnesyl protein transferase; the indicated concentration of tricyclic compound or dimethylsulfoxide (DMSO) vehicle control (5% DMSO final); and 5 mM Ras-CVLS in a total volume of 100 ml. The reaction was allowed to proceed for 30 minutes at room temperature and then stopped with 0.5 ml of 4% sodium dodecyl sulfate (SDS) followed by 0.5 ml of cold 30% trichloracetic acid (TCA). Samples were allowed to sit on ice for 45 minutes and precipitated Ras protein was then collected on GF/C filter paper mats using a Brandel cell harvester. Filter mats were washed once with 6% TCA, 2% SDS and radioactivity was measured in a Wallac 1204 Betaplate BS liquid scintillation counter. Percent inhibition was calculated relative to the DMSO vehicle control.

The geranylgeranyl protein transferase I assay was essentially identical to the farnesyl protein transferase assay described above, with two exceptions: [³H]geranylgeranyl pyrophosphate replaced farnesyl pyrophosphate as the isoprenoid donor and Ras-CVLL was the protein acceptor. This is similar to the assay reported by Casey et al (Casey, P. J., et al., (1991), Enzymatic modification of proteins with a geranylgeranyl isoprenoid, Proc. Natl. Acad. Sci, USA 88: 8631–8635, the disclosure of which is incorporated herein by reference thereto).

2. Cell-Based Assay

Transient expression of val$^{12}$-Ha-Ras-CVLS and val$^{12}$-Ha-Ras-CVLL in COS monkey kidney cells: Effect of farnesyl protein transferase inhibitors on Ras processing and on disordered cell growth induced by transforming Ras.

COS monkey kidney cells were transfected by electroporation with the plasmid pSV-SPORT (Gibco/BRL) containing a cDNA insert encoding either Ras-CVLS or Ras-CVLL, leading to transient overexpression of a Ras substrate for either farnesyl protein transferase or geranylgeranyl protein transferase I, respectively (see above).

Following electroporation, cells were plated into 6-well tissue culture dishes containing 1.5 ml of Dulbecco's-modified Eagle's media (GIBCO, Inc.) supplemented with 10% fetal calf serum and the appropriate farnesyl protein transferase inhibitors. After 24 hours, media was removed and fresh media containing the appropriate drugs was re-added.

48 hours after electroporation cells were examined under the microscope to monitor disordered cell growth induced by transforming Ras. Cells expressing transforming Ras become more rounded and refractile and overgrow the monolayer, reminiscent of the transformed phenotype. Cells were then photographed, washed twice with 1 ml of cold phosphate-buffered saline (PBS) and removed from the dish by scraping with a rubber policeman into 1 ml of a buffer containing 25 mM Tris, pH 8.0; 1 mM ethylenediamine tetraacetic acid; 1 mM phenylmethylsulfonyl fluoride; 50 mM leupeptin; and 0.1 mM pepstatin. Cells were lysed by homogenization and cell debris was removed by centrifugation at 2000×g for 10 min.

Cellular protein was precipitated by addition of ice-cold trichloroacetic acid and redissolved in 100 ml of SDS-electrophoresis sample buffer. Samples (5–10 ml) were loaded onto 14% polyacrylamide minigels (Novex, Inc.) and electrophoresed until the tracking dye neared the bottom of the gel. Proteins resolved on the gels were electroblotted onto nitrocellulose membranes for immunodetection.

Membranes were blocked by incubation overnight at 4° C. in PBS containing 2.5% dried milk and 0.5% Tween-20 and then incubated with a Ras-specific monoclonal antibody, Y13-259 (Furth, M. E., et al., (1982), Monoclonal antibodies to the p21 products of the transforming gene of Harvey murine sarcoma virus and of the cellular ras gene family, J. Virol. 43: 294–304), in PBS containing 1% fetal calf serum for one hour at room temperature. After washing, membranes were incubated for one hour at room temperature with a 1:5000 dilution of secondary antibody, rabbit anti-rat 1gG conjugated to horseradish peroxidase, in PBS containing 1% fetal calf serum. The presence of processed and unprocessed Ras-CVLS or Ras-CVLL was detected using a colorimetric peroxidase reagent (4-chloro-1-naphthol) as described by the manufacturer (Bio-Rad).

3. Cell Mat Assay

Normal human HEPM fibroblasts were planted in 3.5 cm dishes at a density of 5×10$^4$ cells/dish in 2 ml growth medium, and incubated for 3–5d to achieve confluence. Medium was aspirated from each dish and the indicator tumor cells, T24-BAG4 human bladder carcinoma cells expressing an activated H-ras gene, were planted on top of the fibroblast monolayer at a density of 2×10$^3$cells/dish in 2 ml growth medium, and allowed to attach overnight. Compound-induced colony inhibition was assayed by addition of serial dilutions of compound directly to the growth medium 24 h after tumor cell planting, and incubating cells for an additional 14 d to allow colony formation. Assays were terminated by rinsing monolayers twice with phosphate-buffered saline (PBS), fixing the monolayers with a 1% glutaraldehyde solution in PBS, then visualizing tumor cells by staining with X-Gal (Price, J., et al., Lineage analysis in the vertebrate nervous system by retrovirus-mediated gene transfer, Proc. Natl. Acad. Sci.84, 156–160 (1987)). In the colony inhibition assay, compounds were evaluated on the basis of two IC$_{50}$ values: the concentration of drug required to prevent the increase in tumor cell number by 50% (tICso) and the concentration of drug required to reduce the density of cells comprising the cell mat by 50% (mICr$_{so}$). Both IC$_{50}$ values were obtained by determining the density of tumor cells and mat cells by visual inspection and enumeration of cells per colony and the number of colonies under the microscope. The therapeutic index of the compound was quantitatively expressed as the ratio of mIC$_{50}$/tIC$_{50}$, with values greater than one indicative of tumor target specificity.

TABLE 2

| | FPT INHIBITION | |
|---|---|---|
| COMPOUND | FPT IC$_{50}$ (µM) | COS IC$_{50}$ (µM) |
| E-1 | <0.45; 0.52 | — |
| E-1A | — | — |
| E-1B | 3.3 | — |
| E-2 | 0.59 | >5 |
| E-2A | — | — |
| E-2B | — | — |
| E-2C | 2.8 | — |
| E-3 | 6.9 | — |
| E-3A | 11% (14 µM) | — |
| E-3B | 33% (50 µM) | — |
| E-3C | 8.0 | — |
| E-3D | >13.9 | — |
| E-3J | 5.1 | — |
| E-3K | >14 | — |
| E-3L | >45 | — |

TABLE 2-continued

FPT INHIBITION

| COMPOUND | FPT IC$_{50}$ ($\mu$M) | COS IC$_{50}$ ($\mu$M) |
|---|---|---|
| E-3H | — | — |
| E-2P | 3.3 | — |
| E-4B | 8.8 | — |
| E-2Q | >40 | — |
| E-1J | 4.8 | — |
| E-2R | >42 | — |
| E-2T | 33.5 | — |
| E-2S | >43 | — |
| E-1K | >34 | — |
| E-3E | 7.8 | — |
| E-3F | >14 | — |
| E-7A | >14.4 | — |
| E-7B | >14.0 | — |
| E-6 | >13 | — |
| E-2E | 0.71 | 2.5 |
| E-3G | >45 | — |
| E-2M | 15% (15 $\mu$M) | — |
| E-7 | inactive | — |
| E-1G | <0.44 | — |
| E-2J | >39.4 | — |
| E-2H | 1.34 | — |
| E-2G | 33% (42 $\mu$M) | — |
| E-2F | 33% (42 $\mu$M) | — |
| E-4 | 0.97 | — |
| E-1H | 0.19 | — |
| E-2K | >13 | — |
| E-2L | >12 | — |
| E-2N | >13 | — |
| E-5 | >14 | — |
| E-1D | 0.84 | — |
| E-2D | 0.58 | — |
| E-2U | 6.4 | — |
| E-2V | 44.0 | — |
| E-4A | 7.5 | — |
| E-3N | 4.2 | — |
| E-3M | 37% (14 $\mu$M) | — |

TABLE 3

COMPARISON OF FPT INHIBITION AND GGPT INHIBITION

| COMPOUND | ENZYME INHIBITION FPT IC$_{50}$ $\mu$M | ENZYME INHIBITION GGPT IC$_{50}$ $\mu$M |
|---|---|---|
| E-2E | 0.71 | 7.4 mM |
| E-1G | 0.47 | <13 |

TABLE 4

INHIBITION OF TUMOR CELL GROWTH - MAT ASSAY

| COMPOUND | INHIBITION OF TUMOR CELL GROWTH (IC$_{50}$ $\mu$M) | INHIBITION OF NORMAL CELL GROWTH (IC$_{50}$ $\mu$M) |
|---|---|---|
| E-2E | <3.1 | >50 |
| E-1G | 12.5 | >25 |
| E-2H | 12.5 | >25 |

RESULTS

1. Enzymology

The data demonstrate that the compounds of the invention are inhibitors of Ras-CVLS farnesylation by partially purified rat and human brain farnesyl protein transferase (FPT). The data also show that there are compounds of the invention which can be considered as potent (IC$_{50}$<10 $\mu$M) inhibitors of Ras-CVLS farnesylation by partially purified rat brain farnesyl protein transferase (FPT)—see Table 3.

The data also demonstrate that compounds of the invention are poorer inhibitors of geranylgeranyl protein transferase (GGPT) assayed using Ras-CVLL as isoprenoid acceptor. Tested compounds were inactive or weakly active as geranylgeranyl transferase inhibitors at 20 $\mu$g/ml. This selectivity is important for the therapeutic potential of the compounds used in the methods of this invention, and increases the potential that the methods of this invention, and increases the potential that the compounds will have selective growth inhibitory properties against Ras-transformed cells.

2. Cell-Based: COS Cell and Cell Mat Assays

Immunoblot analysis of the Ras protein expressed in Ras-transfected COS cells indicated that the farnesyl transferase inhibitors of this invention inhibit Ras-CVLS processing, causing accumulation of unprocessed Ras (Table 3). For example, compounds E-2 and E-2E inhibit Ras-CVLS processing with IC$_{50}$ values of >5 and 2.5 $\mu$M, respectively. These results show that the compounds inhibit farnesyl protein transferase in intact cells and indicate their potential to block cellular transformation by activated Ras oncogenes.

Compounds of this invention also inhibited the growth of Ras-transformed tumor cells in the Mat assay. For example, compound E-2E inhibited with an IC$_{50}$ value of <3.1 $\mu$M. This compound only displayed cytotoxic activity against the normal cell monolayer at higher concentrations (IC$_{50}$ of >50 $\mu$M).

In Vivo Anti-Tumor Studies

The anti-tumor activity of compounds of the present invention can also be demonstrated in vivo studies such as the following. Tumor cells (5×10$^5$ to 8×10$^6$ of M27 [mouse Lewis lung carcinoma], A431 [human epidermal carcinoma] or SW620 [human colon adenocarcinoma (lymph node metastasis)]) are innoculated subcutaneously into the flank of 5–6 week old athymic nu/nu female mice. For the C-f-1 [mouse fibroblast transformed with c-fos oncogene] tumor model, 2 mm$^3$ tumor fragments are transplanted subcutaneously into the flank of 5–6 week old athymic nu/nu female mice. Tumor bearing animals are selected and randomized when the tumors are established. Animals are treated with vehicle (beta cyclodextran for i.p. or corn oil for p.o.) only or compounds in vehicle twice a day (BID) for 5 (1–5) or 7 (1–7) days per week for 2 (×2) or 4 (×4) weeks. The percent inhibition of tumor growth relative to vehicle controls are determined by tumor measurements.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms which contain a compound of the invention. The scope of the invention in its pharmaceutical composition aspect is not to be limited by the examples provided.

Pharmaceutical Dosage Form Examples

EXAMPLE A

| No. | Ingredients | mg/tablet | mg/tablet |
|---|---|---|---|
| | Tablets | | |
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B

| No. | Ingredient | mg/capsule | mg/capsule |
|---|---|---|---|
| | Capsules | | |
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A method for inhibiting farnesyl protein transferase in a patient comprising administering an effective amount of a compound of formula (Ia), (Ib) or (Ic)

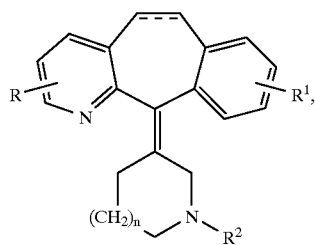

(Ia)

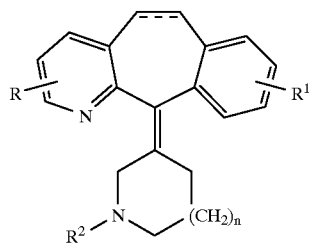

(Ib)

(Ic)

wherein:

R and R¹ are independently selected from H, $(C_1-C_6)$ alkyl, halogeno, OH, $(C_1-C_6)$alkoxy, $NH_2$, $(C_1-C_6)$ alkylamino, di$((C_1-C_6)$alkyl)amino, $CF_3$, $SO_3H$, $CO_2R^3$, $NO_2$, $SO_2NH_2$, and $CONHR^4$;

R² is $R^5SO_2$— wherein R⁵ is heteroaryl and said heteroaryl is selected from 2-pyridyl, 3-pyridyl, 4-pyridyl, 2-pyridyl N-oxide, 3-pyridyl N-oxide or 4-pyridyl N-oxide and wherein said heteroaryl is optionally substituted with 1 to 3 substituents selected from halogeno, $(C_1-C_6)$alkyl, $(C_1-C_6)$alkoxy, amino, alkylamino, dialkylamino, $C_6H_5C(O)NHCH_2$— and —$COOR^8$, wherein R⁸ is H or $(C_1-C_6)$alkyl;

R³ is $(C_1-C_6)$alkyl, aryl;

R⁴ is $(C_1-C_6)$alkyl;

n is 0 or 1; and the dotted line represents an optional double bond;

and pharmaceutically acceptable salts thereof.

2. A compound selected from a compound of the formula (Ia), (Ib) or (Ic)

(Ia)

(Ib)

(Ic)

wherein:

R and R¹ are independently selected from H, $(C_1-C_6)$ alkyl, halogeno, OH, $(C_1-C_6)$alkoxy, $NH_2$, $(C_1-C_6)$ alkylamino, di$((C_1-C_6)$alkyl)amino, $CF_3$, $SO_3H$, $CO_2R^3$, $NO_2$, $SO_2NH_2$, and $CONHR^4$;

R² is $R^5SO_2$— wherein R⁵ is heteroaryl and said heteroaryl is selected from 2-pyridyl, 3-pyridyl, 4-pyridyl, 2-pyridyl N-oxide, 3-pyridyl N-oxide or 4-pyridyl N-oxide and wherein said heteroaryl is optionally substituted with 1 to 3 substituents selected from halogeno, $(C_1-C_6)$alkyl, $(C_1-C_6)$alkoxy, amino, alkylamino, dialkylamino, $C_6H_5C(O)NHCH_2$— and —$COOR^8$, wherein R⁸ is H or $C_1-C_6$)alkyl;

R³ is $(C_1-C_6)$alkyl, aryl;

R⁴ is $(C_1-C_6)$alkyl;

n is 0 or 1; and the dotted line represents an optional double bond;

and pharmaceutically acceptable salts thereof.

3. The compound of claim 2 having the Ostructure (Ib).

4. The compound of claim 2 wherein R and R¹ are indepedently selected from H or halogeno.

5. The compound of claim 4 wherein R⁵ is 4-pyridyl or 3-pyridyl.

6. The compound of claim 3 wherein R⁵ is 3-pyridyl.

7. The compound of claim 3 having the structural formula

8. A pharmaceutical composition comprising a pharmaceutically acceptable carrier and an effective amount of a compound of claim 2.

* * * * *